US 9,221,819 B2

(12) United States Patent
Dhar et al.

(10) Patent No.: US 9,221,819 B2
(45) Date of Patent: Dec. 29, 2015

(54) SPIROCYCLIC COMPOUNDS AS MODULATORS OF CHEMOKINE RECEPTOR ACTIVITY

(71) Applicant: BRISTOL-MYERS SQUIBB COMPANY, Princeton, NJ (US)

(72) Inventors: T. G. Murali Dhar, Newtown, PA (US); John V. Duncia, Newtown, PA (US); Daniel S. Gardner, Furlong, PA (US); Weiwei Guo, Ewing, NJ (US); John Hynes, Washington Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/503,456

(22) Filed: Oct. 1, 2014

(65) Prior Publication Data
US 2015/0018347 A1 Jan. 15, 2015

Related U.S. Application Data

(62) Division of application No. 13/500,323, filed as application No. PCT/US2010/051577 on Oct. 6, 2010, now Pat. No. 8,877,749.

(60) Provisional application No. 61/249,364, filed on Oct. 7, 2009.

(51) Int. Cl.
*C07D 471/10* (2006.01)
*A61K 31/4427* (2006.01)
*C07D 401/12* (2006.01)
*C07D 405/12* (2006.01)
*C07D 413/12* (2006.01)
*C07D 471/04* (2006.01)

(52) U.S. Cl.
CPC .......... *C07D 471/10* (2013.01); *A61K 31/4427* (2013.01); *C07D 401/12* (2013.01); *C07D 405/12* (2013.01); *C07D 413/12* (2013.01); *C07D 471/04* (2013.01)

(58) Field of Classification Search
CPC .. C07D 401/12; C07D 405/12; C07D 413/12; C07D 471/04; A61K 31/4427
USPC .............. 544/71, 231; 546/15, 18; 514/228.8, 514/274, 278
See application file for complete search history.

(56) References Cited

U.S. PATENT DOCUMENTS

| 7,601,844 B2 * | 10/2009 | Carter et al. ................ 546/228 |
| 8,633,226 B2 | 1/2014 | Santella |
| 8,642,622 B2 | 2/2014 | Cherney et al. |
| 2012/0202802 A1 | 8/2012 | Dhar et al. |

FOREIGN PATENT DOCUMENTS

| WO | WO 2007/092681 | 8/2007 |
| WO | WO 2009/015164 | 1/2009 |
| WO | WO 2009/015166 | 1/2009 |

OTHER PUBLICATIONS

Carson, K.G. et al., "CCR1 Antagonists", Annual Reports in Medicinal Chemistry, vol. 39, pp. 149-158 (2004).
Carter, P.H., "Chemokine receptor antagonism as an approach to anti-inflammatory therapy: 'just right' or plain wrong?", Current Opinion in Chemical Biology, vol. 6, pp. 510-525 (2002).
Cohen, M.C. et al., "Cytokine Function: A Study in Biologic Diversity", Am. J. Clin. Pathol., vol. 105, No. 5, pp. 589-598 (1996).
Horuk, R. et al., "CCR1-specific non-peptide antagonist: efficacy in a rabbit allograft rejection model", Immunology Letters, vol. 76, pp. 193-201 (2001).
Jensen, P.C. et al., Chapter 8: "Activation Mechanisms of Chemokine Receptors", Methods in Enzymology, vol. 461, pp. 171-190, Elsevier Inc., publ. (2009).
Lee, M.M.K. et al., "CCR1-mediated activation of nuclear factor-κB in THP-1 monocytic cells involves *pertussis* toxin-insensitive $G\alpha_{14}$ and $G\alpha_{16}$ signaling cascades", Journal of Leukocyte Biology, vol. 86, pp. 1319-1329 (2009).
Lee, S.C. et al., "Cutaneous Injection of Human Subjects with Macrophage Inflammatory Protein-1α Induces Significant Recruitment of Neutrophils and Monocytes", The Journal of Immunology, vol. 164, pp. 3392-3401 (2000).

(Continued)

*Primary Examiner* — Celia Chang
(74) *Attorney, Agent, or Firm* — Hong Liu

(57) ABSTRACT

The present application describes modulators of chemokine receptor activity of formula I (I)

or stereoisomers or pharmaceutically acceptable salts thereof. In addition, methods of treating and preventing inflammatory diseases such as asthma and allergic diseases, as well as autoimmune pathologies such as rheumatoid arthritis and transplant rejection using modulators of formula (I) are disclosed.

2 Claims, No Drawings

(56) References Cited

OTHER PUBLICATIONS

Premack, B.A. et al., "Chemokine receptors: Gateways to inflammation and infection", Nature Medicine, vol. 2, No. 11, pp. 1174-1178 (1996).

Saunders, J. et al., "Opportunities for novel therapeutic agents acting at chemokine receptors", Drug Discovery Today, vol. 4, No. 2, pp. 80-92 (1999).

Trivedi, B.K. et al., Chapter 17: "Chemokines: Targets for Novel Therapeutics", Annual Reports in Medicinal Chemistry, vol. 35, Academic Press, publ., pp. 191-200 (2000).

* cited by examiner

SPIROCYCLIC COMPOUNDS AS MODULATORS OF CHEMOKINE RECEPTOR ACTIVITY

CROSS-REFERENCE TO RELATED APPLICATIONS

This application is a Divisional of U.S. patent application Ser. No. 13/500,323, filed on Apr. 5, 2012, which is a U.S. national phase of International Application No. PCT/US2010/051577, filed on Oct. 6, 2010, which claims priority of U.S. Ser. No. 61/249,364, filed Oct. 7, 2009, incorporated by reference herein in their entirety.

FIELD OF THE INVENTION

This invention relates generally to spirocyclic compounds as modulators of chemokine receptor activity, pharmaceutical compositions containing the same, and methods of using the same as an agent for treatment and prevention of inflammatory diseases, allergic and autoimmune diseases, and in particular, rheumatoid arthritis and transplant rejection.

BACKGROUND OF THE INVENTION

Chemokines are chemotactic cytokines, of molecular weight 6-15 kDa, that are released by a wide variety of cells to attract and activate, among other cell types, monocytes, macrophages, T and B lymphocytes, eosinophils, basophils and neutrophils. There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils.

The chemokines bind to specific cell-surface receptors belonging to the family of G-protein-coupled seven-transmembrane-domain proteins which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] CCR-2A and CCR-2B (or "CKR-2A"/"CKR-2B" or "CC-CKR-2A"/"CC-CKR-2B") [MCP-1, MCP-2, MCP-3, MCP-4, MCP-5];CCR-3 (or "CKR-3" or "CC-CKR-3") [eotaxin-1, eotaxin-2, RANTES, MCP-3, MCP-4]; CCR-4 (or "CKR-4" or "CC-CKR-4") [TARC, MDC]; CCR-5 (or "CKR-5" OR "CC-CKR-5") [MIP-1α, RANTES, MIP-1β]; CCR-6 (or "CKR-6" or "CC-CKR-6") [LARC]; CCR-7 (or "CKR-7" or "CC-CKR-7") [ELC]; CCR-8 (or "CKR-8" or "CC-CKR-8") [I-309]; CCR-10 (or "CKR-10" or "CC-CKR-10") [MCP-1, MCP-3]; and CCR-11 [MCP-1, MCP-2, and MCP-4].

In addition to the mammalian chemokine receptors, mammalian cytomegaloviruses, herpesviruses and poxviruses have been shown to express, in infected cells, proteins with the binding properties of chemokine receptors. Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and arthrosclerosis (reviewed in: Carter, P. H., *Current Opinion in Chemical Biology* 2002, 6, 510; Trivedi et al., *Ann. Reports Med. Chem.* 2000, 35, 191; Saunders et al., *Drug Disc. Today* 1999, 4, 80; Premack et al., *Nature Medicine* 1996, 2, 1174). For example, the chemokine macrophage inflammatory protein-1 (MIP-1α) and its receptor CC Chemokine Receptor 1 (CCR-1) play a pivotal role in attracting leukocytes to sites of inflammation and in subsequently activating these cells. When the chemokine MIP-1α binds to CCR-1, it induces a rapid increase in intracellular calcium concentration, increased expression of cellular adhesion molecules, cellular degranulation, and the promotion of leukocyte migration.

In addition, demonstration of the chemotactic properties of MIP-1α in humans has been provided experimentally. Human subjects, when injected intradermally with MIP-1α, experienced a rapid and significant influx of leukocytes to the site of injection (Brummet, M. E., *J. Immun.* 2000, 164, 3392-3401).

Demonstration of the importance of the MIP-1α/CCR-1 interaction has been provided by experiments with genetically modified mice. MIP-1α -/- mice had normal numbers of leukocytes, but were unable to recruit monocytes into sites of viral inflammation after immune challenge. Recently, MIP-1α -/- mice were shown to be resistant to collagen antibody induced arthritis. Likewise, CCR-1 -/- mice were unable to recruit neutrophils when challenged with MIP-1α in vivo; moreover, the peripheral blood neutrophils of CCR-1 null mice did not migrate in response to MIP-1α, thereby demonstrating the specificity of the MIP-1α/CCR-1 interaction. The viability and generally normal health of the MIP-1α -/- and CCR-1 -/- animals is noteworthy, in that disruption of the MIP-1α/CCR-1 interaction does not induce physiological crisis. Taken together, these data lead one to the conclusion that molecules that block the actions of MIP-1α would be useful in treating a number of inflammatory and autoimmune disorders. This hypothesis has now been validated in a number of different animal disease models, as described below.

It is known that MIP-1α is elevated in the synovial fluid and blood of patients with rheumatoid arthritis. Moreover, several studies have demonstrated the potential therapeutic value of antagonism of the MIP-1α/CCR1 interaction in treating rheumatoid arthritis.

It should also be noted that CCR-1 is also the receptor for the chemokines RANTES, MCP-3, HCC-1, Lkn-1/HCC-2, HCC-4, and MPIF-1 (Carter, P. H., *Curr. Opin Chem. Bio.* 2002, 6, 510-525). Since it is presumed that the new compound of formula (I) described herein antagonizes MIP-1α by binding to the CCR-1 receptor, it may be that this compound is also an effective antagonist of the actions of the aforementioned ligand that are mediated by CCR-1. Accordingly, when reference is made herein to "antagonism of MIP-1α," it is to be assumed that this is equivalent to "antagonism of chemokine stimulation of CCR-1."

Recently, a number of groups have described the development of small molecule antagonists of MIP-1α (reviewed in: Carson, K. G. et al., *Ann. Reports Med. Chem.* 2004, 39, 149-158).

SUMMARY OF THE INVENTION

Accordingly, the present invention provides novel antagonists or partial agonists/antagonists of MIP-1α or CCR-1 receptor activity of the formula

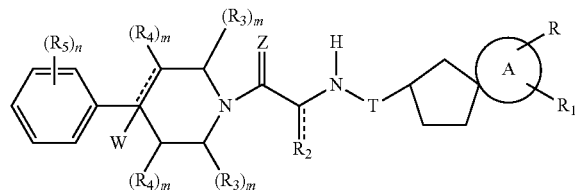

or stereoisomers or pharmaceutically acceptable salts thereof.

The present invention provides pharmaceutical compositions comprising a pharmaceutically acceptable carrier and a therapeutically effective amount of at least one of the compounds of the present invention or a pharmaceutically acceptable salt form thereof.

The present invention provides a method for treating rheumatoid arthritis and transplant rejection, comprising administering to a host in need of such treatment a therapeutically effective amount of at least one of the compounds of the present invention or a pharmaceutically acceptable salt form thereof.

The present invention provides a method for treating inflammatory diseases, comprising administering to a host in need of such treatment a therapeutically effective amount of at least one of the compounds of the present invention or a pharmaceutically acceptable salt form thereof.

The present invention provides novel spirocyclic compounds for use in therapy.

The present invention provides the use of novel spirocyclic compounds for the manufacture of a medicament for the treatment of inflammatory diseases.

DETAILED DESCRIPTION OF THE PRESENT INVENTION

In one embodiment, the present invention provides novel compounds of formula (I):

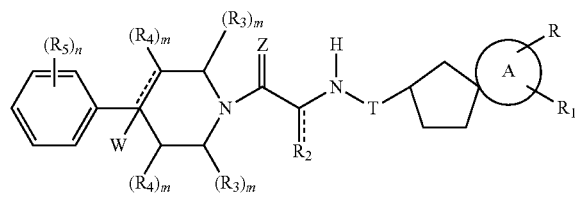

or stereoisomers or pharmaceutically acceptable salt forms thereof, wherein:
the dashed line represents an optional double bond;
Ring A is an optionally substituted three to nine membered mono- or bicyclic heterocyclic ring;
T is

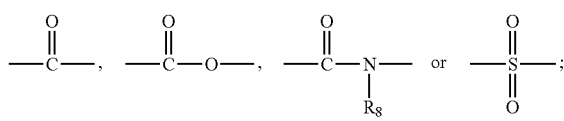

W is —OH;
Z is a O or S;
R and $R_1$ are independently hydrogen, alkyl, halo, C=O or —COalkyl;
$R_2$ is hydrogen, alkyl or cycloalkyl;
$R_3$, at each occurrence, are independently hydrogen or alkyl;
$R_4$, at each occurrence, are independently hydrogen, halo, hydroxy or alkyl;
$R_5$, at each occurrence, is hydrogen, halo, alkyl or cycloalkyl;
m, at each occurrence, is 0-2; and
n, at each occurrence, is 0-2.

In another embodiment, compounds of the present invention, or a stereoisomer or pharmaceutically acceptable salt from thereof, are those in which the compound is a compound of formula (Ia):

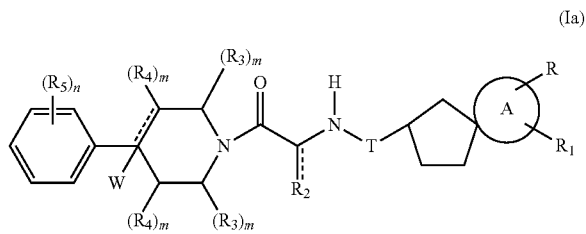

wherein
Ring A is an optionally substituted five to seven membered heterocyclic ring;
T is

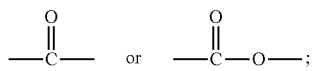

W is —OH;
R and $R_1$ are independently hydrogen, alkyl, halo, C=O or —COalkyl;
$R_2$ is $C_1$-$C_4$alkyl or cycloalkyl;
$R_3$, at each occurrence, are independently hydrogen or alkyl;
$R_4$, at each occurrence, are independently hydroxy or $C_1$-$C_4$alkyl;
$R_5$, at each occurrence, is a halogen atom;
m, at each occurrence, is 0-2; and
n, at each occurrence, is 0-2.

In still yet another embodiment, compounds of the present invention, or a stereoisomer or pharmaceutically acceptable salt from thereof, are those of compound Ib:

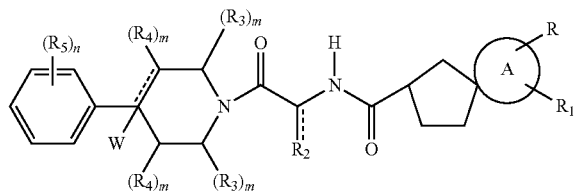

wherein
Ring A is an optionally substituted five to six membered heterocyclic ring;
R and $R_1$ are independently hydrogen, alkyl, halo, C=O or —COalkyl;
$R_2$ is $C_1$-$C_4$alkyl;
$R_3$, at each occurrence, are independently hydrogen or alkyl;
$R_4$, at each occurrence, are independently $C_1$-$C_4$alkyl;
$R_5$, at each occurrence, is —Cl;
m, at each occurrence, is 0-2; and
n, at each occurrence, is 0-2.

Representative compounds of the invention include the following:
(2R)-N-((R)-1-((S)-4-(4-chlorophenyl)-4-hydroxy-3,3-dimethylpiperidin-1-yl)-3-methyl-1-oxobutan-2-yl)-7-oxo-8-oxa-6-azaspiro[4.5]decane-2-carboxamide,
(2R)-N-((R)-1-((S)-4-(4-chlorophenyl)-4-hydroxy-3,3-dimethylpiperidin-1-yl)-3-methyl-1-oxobutan-2-yl)-7-oxo-6,8-diazaspiro[4.5]decane-2-carboxamide,
N-((R)-1-((S)-4-(4-chlorophenyl)-4-hydroxy-3,3-dimethylpiperidin-1-yl)-3-methyl-1-oxobutan-2-yl)-7-oxo-6-oxa-8-azaspiro[4.5]decane-1-carboxamide,
(7R)-N-((R)-1-((S)-4-(4-chlorophenyl)-4-hydroxy-3,3-dimethylpiperidin-1-yl)-3-methyl-1-oxobutan-2-yl)-2-oxo-1-oxa-3-azaspiro[4.4]nonane-7-carboxamide;
(2R)-N-((R)-1-((S)-4-(4-chlorophenyl)-4-hydroxy-3,3-dimethylpiperidin-1-yl)-3-methyl-1-oxobutan-2-yl)-7-oxo-6-oxa-8-azaspiro[4.5]decane-2-carboxamide
(3R)-N-((R)-1-((S)-4-(4-chlorophenyl)-4-hydroxy-3,3-dimethylpiperidin-1-yl)-3-methyl-1-oxobutan-2-yl)-3'-methyl-6'-oxo-2',5',6',7'-tetrahydro-spiro[cyclopentane-1,4'-pyrazolo[3,4-b]pyridine]-3-carboxamide,
(7R)-N-((R)-1-((S)-4-(4-chlorophenyl)-4-hydroxy-3,3-dimethylpiperidin-1-yl)-3-methyl-1-oxobutan-2-yl)-2,4-dioxo-1,3-diazaspiro[4.4]nonane-7-carboxamide,
(7R)-N-((R)-1-((S)-4-(4-chlorophenyl)-4-hydroxy-3,3-dimethylpiperidin-1-yl)-3-methyl-1-oxobutan-2-yl)-1-methyl-2,4-dioxo-1,3-diazaspiro[4.4]nonane-7-carboxamide,
(7R)-3-chloro-N-((R)-1-((S)-4-(4-chlorophenyl)-4-hydroxy-3,3-dimethylpiperidin-1-yl)-3-methyl-1-oxobutan-2-yl)-1-azaspiro[4.4]nonane-7-carboxamide,
(7R)-1-acetyl-N-((R)-1-((S)-4-(4-chlorophenyl)-4-hydroxy-3,3-dimethylpiperidin-1-yl)-3-methyl-1-oxobutan-2-yl)-1-azaspiro[4.4]nonane-7-carboxamide,
N-((R)-1-((S)-4-(4-Chlorophenyl)-4-hydroxy-3,3-dimethylpiperidin-1-yl)-3-methyl-1-oxobutan-2-yl)-1-oxaspiro[2.4]heptane-5-carboxamide, and
N-((R)-1-((S)-4-(4-Chlorophenyl)-4-hydroxy-3,3-dimethylpiperidin-1-yl)-3-methyl-1-oxobutan-2-yl)-1-oxaspiro[3.4]octane-6-carboxamide.

In another embodiment, the present invention is directed to a pharmaceutical composition, comprising a pharmaceutically acceptable carrier and a therapeutically effective amount of a compound of the present invention.

In another embodiment, the present invention is directed to a method for modulation of chemokine or chemokine receptor activity comprising administering to a patient in need thereof a therapeutically effective amount of a compound of the present invention.

In another embodiment, the present invention is directed to a method for modulation of CCR-1 receptor activity comprising administering to a patient in need thereof a therapeutically effective amount of a compound of the present invention.

In another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of a compound of the present invention.

In another embodiment, the present invention is directed to a method for treating disorders, comprising administering to a patient in need thereof a therapeutically effective amount of a compound of the present invention, said wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a method for treating inflammatory diseases, for example, inflammatory diseases which are at least partially mediated by CCR-1, comprising administering to a patient in need thereof a therapeutically effective amount of a compound of the present invention.

In another embodiment, the present invention is directed to a method for modulation of CCR1 activity comprising administering to a patient in need thereof a therapeutically effective amount of a compound of the present invention.

In another embodiment, the present invention is directed the use of a compound of the present invention in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a compound of the present invention for use in therapy.

In another embodiment, the present invention is directed to a pharmaceutical composition comprising a compound of the present invention and one or more active ingredients.

In another embodiment, the present invention is directed to a method for modulation of chemokine or chemokine receptor activity comprising administering to a patient in need thereof a therapeutically effective amount of a pharmaceutical composition comprised of a compound of the present invention and one or more active ingredients.

In another embodiment, the present invention is directed to a method for modulation of CCR-1 receptor activity comprising administering to a patient in need thereof a therapeutically effective amount of a pharmaceutical composition comprised of a compound of the present invention and one or more active ingredients.

In yet another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of a pharmaceutical composition comprised of a compound of the present invention and one or more active ingredients.

In another embodiment, the present invention is directed to a method for treating a disorder, comprising administering to a patient in need thereof a therapeutically effective amount of a pharmaceutical composition comprised of a compound of the present invention and one or more active ingredients, wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In yet another embodiment, the present invention, is directed to a method for treating inflammatory diseases, preferably, inflammatory diseases which are at least partially mediated by CCR-1, comprising administering to a patient in need thereof a therapeutically effective amount of a pharmaceutical composition comprised of a compound of present invention and one or more active ingredients.

In another embodiment, the present invention is directed to a method for modulation of CCR-1 activity comprising administering to a patient in need thereof a therapeutically effective amount of a pharmaceutical composition comprised of a compound of the present invention and one or more active ingredients.

In another embodiment, the present invention is directed to the use of a pharmaceutical composition comprised of a compound of the present invention and one or more active ingredients in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In still yet another embodiment, the present invention is directed to the use of a pharmaceutical composition comprised of a compound of the present invention and one or more active ingredients in therapy.

In another embodiment, the present invention provides a compound of the present invention for use in therapy for treating an inflammatory disease.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment of an inflammatory disease.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of an inflammatory disease.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat an inflammatory disease.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

The following are definitions of terms that may be used in the specification. The initial definition provided for a group or term herein applies to that group or term throughout the specification individually or as part of another group, unless otherwise indicated.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Young, S. D. et al., *Antimicrobial Agents and Chemotherapy*, 2602-2605 (1995).

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl, any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen.

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings
for example

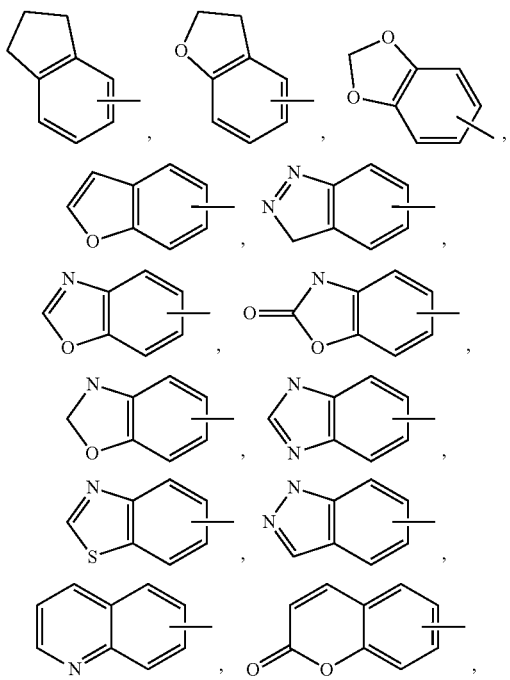

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, or 4-diarylalkyl-1-piperazinyl, all of which may be optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl, benzimidazolyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4- thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazinyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.
The term "nitro" as used herein, refers to an —NO$_2$ group.
The term "hydroxy" as used herein, refers to an OH group.
The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmidic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., publ., p. 1418 (1985), the disclosure of which is hereby incorporated by reference.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Any compound that can be converted in vivo to provide the bioactive agent (i.e., the compound of formula I) is a prodrug within the scope and spirit of the invention.

The term "prodrugs" as employed herein includes esters, carbamates and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:
 a) Wermuth, C. G. et al., *The Practice of Medicinal Chemistry,* Ch. 31, Academic Press, publ. (1996);
 b) Bundgaard, H., ed., *Design of Prodrugs,* Elsevier, publ. (1985);
 c) Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways,* CRC Press, Inc., publ., Ruffolo, Jr., R. R. et al., eds., pp. 173-198 (1995); and d) Testa, B. et al., *Hydrolysis in Drug and Prodrug Metabolism*, Wiley-VCH, publ. (2003).

These references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MIP-1α or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

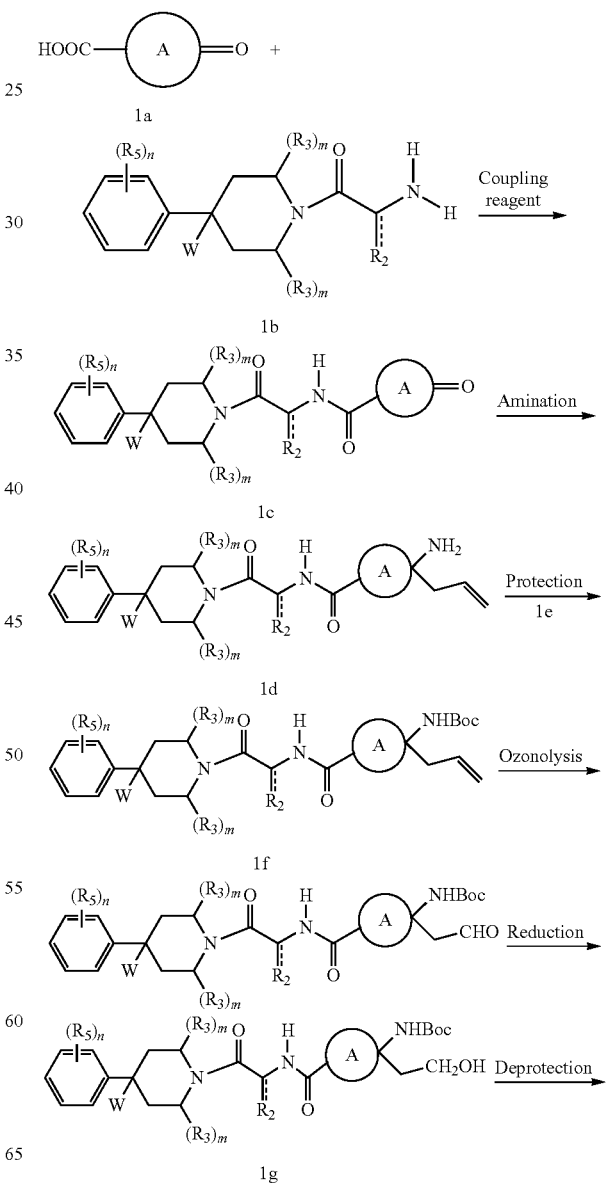

Scheme 1

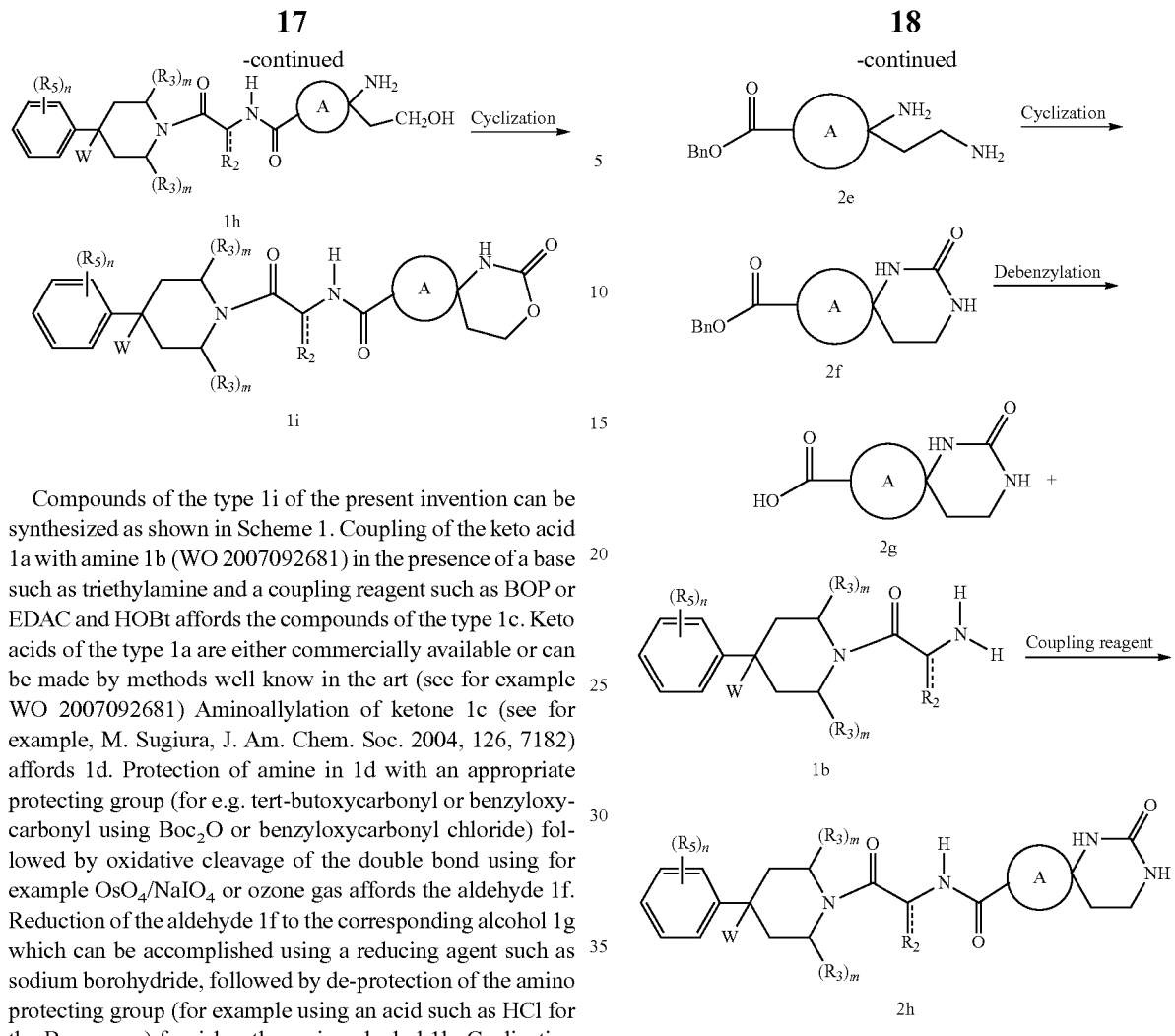

Compounds of the type 1i of the present invention can be synthesized as shown in Scheme 1. Coupling of the keto acid 1a with amine 1b (WO 2007092681) in the presence of a base such as triethylamine and a coupling reagent such as BOP or EDAC and HOBt affords the compounds of the type 1c. Keto acids of the type 1a are either commercially available or can be made by methods well know in the art (see for example WO 2007092681) Aminoallylation of ketone 1c (see for example, M. Sugiura, J. Am. Chem. Soc. 2004, 126, 7182) affords 1d. Protection of amine in 1d with an appropriate protecting group (for e.g. tert-butoxycarbonyl or benzyloxycarbonyl using $Boc_2O$ or benzyloxycarbonyl chloride) followed by oxidative cleavage of the double bond using for example $OsO_4/NaIO_4$ or ozone gas affords the aldehyde 1f. Reduction of the aldehyde 1f to the corresponding alcohol 1g which can be accomplished using a reducing agent such as sodium borohydride, followed by de-protection of the amino protecting group (for example using an acid such as HCl for the Boc group) furnishes the amino alcohol 1h. Cyclization using a carbonyl source such as carbonyldiimidazole or dimethylcarbonate affords the corresponding spirocyclic oxazolidinone 1i.

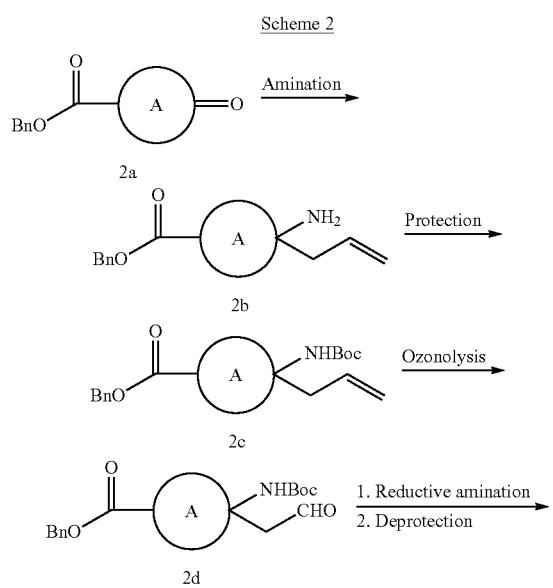

Compounds of the type 2h of the present invention can be synthesized as shown in Scheme 2. Aminoallylation of keto benzyl ester 2a (see for example, M. Sugiura, J. Am. Chem. Soc. 2004, 126, 7182) provides compounds of type 2b. Keto benzyl ester of the type 2a can be made by methods well know in the art (see for example WO 2007092681). Protection of amine in 2b with an appropriate protecting group (for e.g. tert-butoxycarbonyl or benzyloxycarbonyl using $Boc_2O$ or benzyloxycarbonyl chloride) followed by oxidative cleavage of the double bond using for example $OsO_4/NaIO_4$ or ozone gas affords the aldehyde 2d. Reductive amination of 2d (see for example, D. Dube, Tetrahedron Lett. 1999, 40, 2295) followed by de-protection of the amino protecting group (for example using an acid such as HCl for the Boc group) furnishes the diamine 2e. Cyclization using a carbonyl source such as carbonyldiimidazole or dimethylcarbonate affords the corresponding spirocyclic oxazolidinone 2f. Debenzylation of 2f under standard hydrogenation conditions yields the corresponding acid 2g. Coupling of acid 2g with amine 1b (WO 2007092681) in the presence of a base such as triethylamine and a coupling reagent such as BOP or EDAC and HOBt affords compounds of the type 2h.

Scheme 3

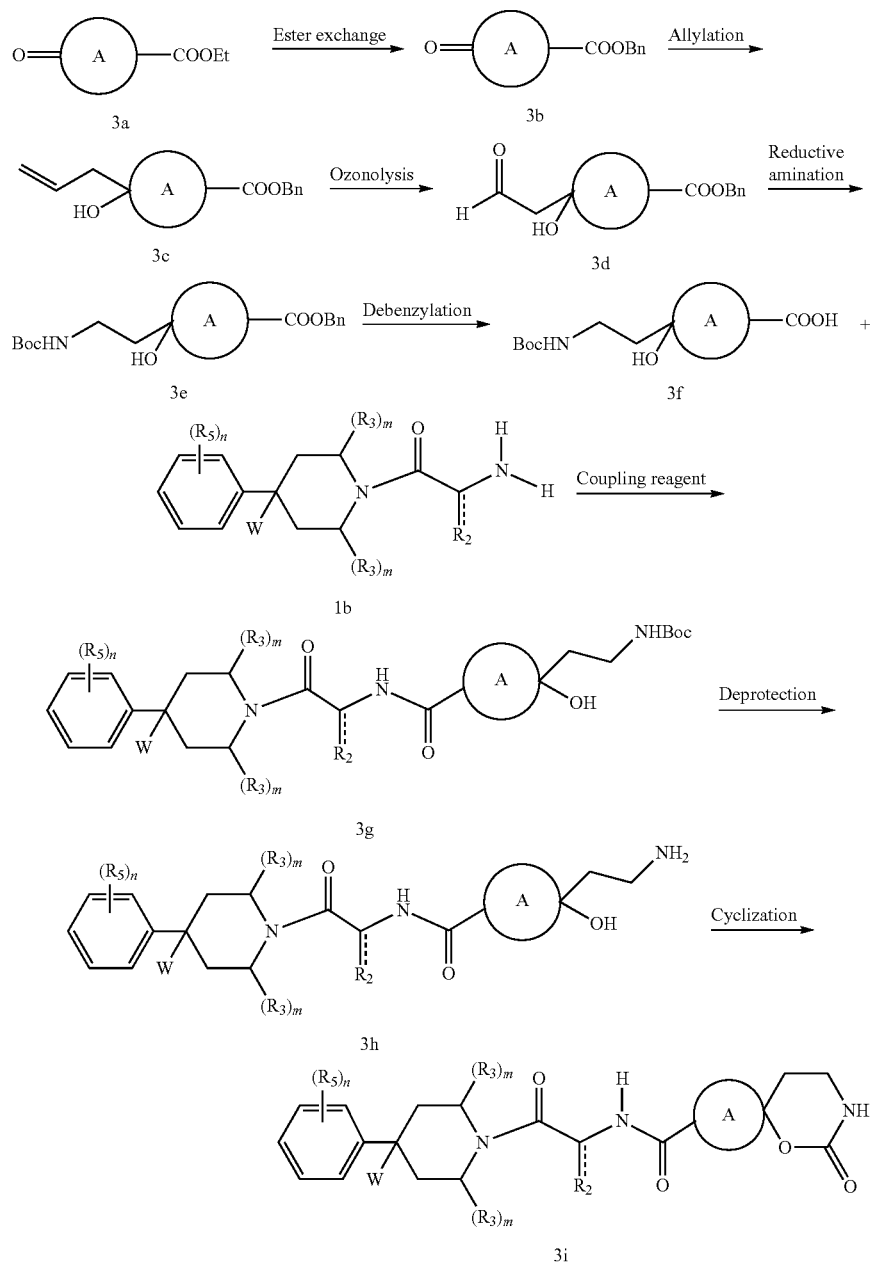

Compounds of the type 3i of the present invention can be synthesized as shown in Scheme 3. Transesterification of keto ethyl ester 3a (see for example, J. Matsuo, Tetrahedron: Asymmetry 2007, 18, 1906) yields the benzyl ester 3b. Keto ethyl ester of type 3a are either commercially available or can be made by methods well known in the art. Allylation of 3b (see for example, C. Li, Tetrahedron 1998, 54, 2347) followed by oxidative cleavage of the double bond using for example $OsO_4/NaIO_4$ or ozone gas affords the aldehyde 3d. Reductive amination of 3d (see for example, D. Dube, Tetrahedron Lett. 1999, 40, 2295) followed by debenzylation under standard hydrogenation conditions affords acid 3f. Coupling of acid 3f with amine 1b (WO 2007092681) in the presence of a base such as triethylamine and a coupling reagent such as BOP or EDAC and HOBt affords 3g. De-protection of the amino protecting group in 3g using an acid such as HCl for the Boc group followed by cyclization using a carbonyl source such as carbonyldiimidazole or dimethylcarbonate affords the corresponding spirocyclic oxazolidinone 3i.

Scheme 4

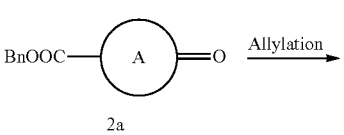

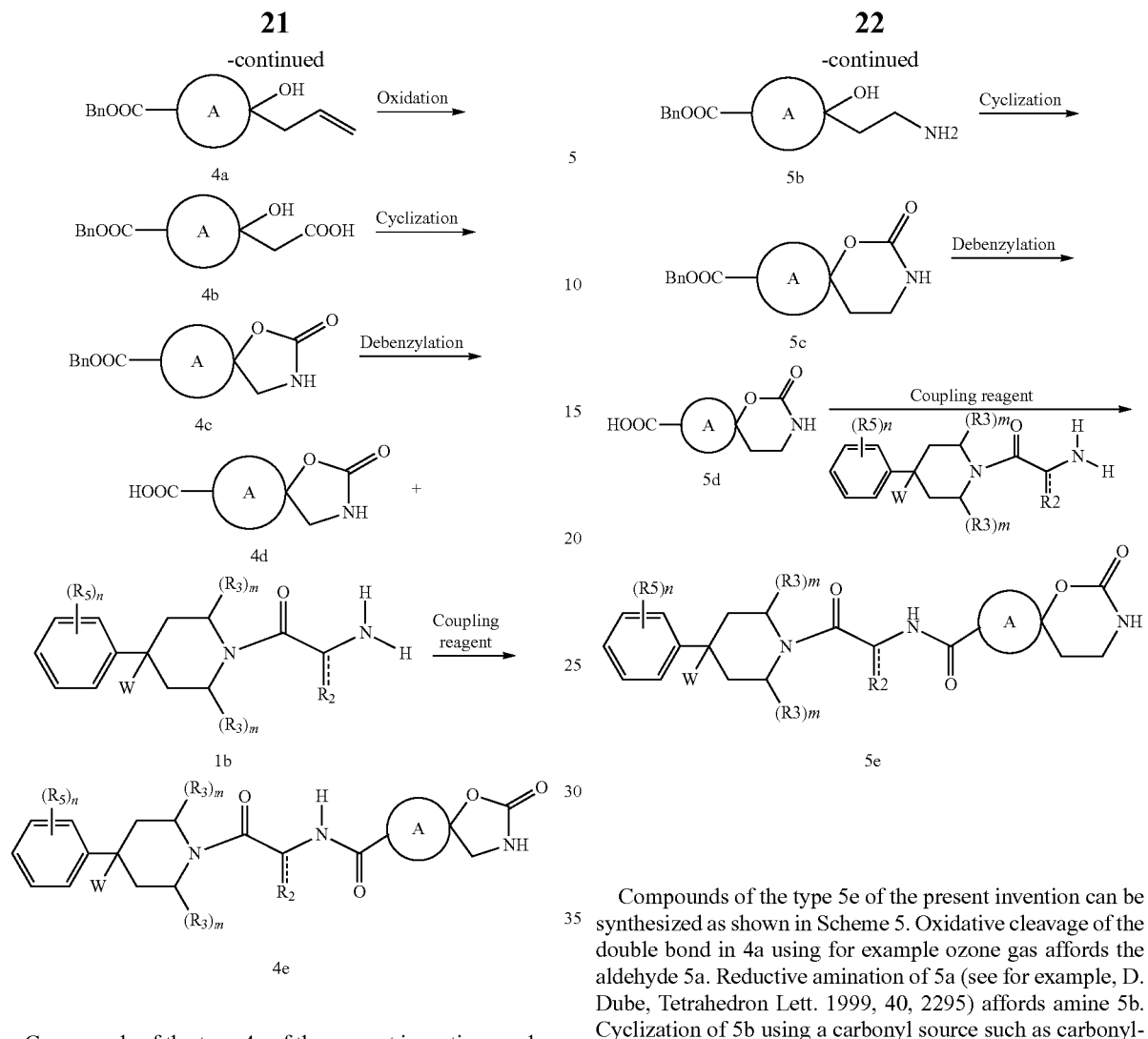

Compounds of the type 4e of the present invention can be synthesized as shown in Scheme 4. Allylation of 2a yields the homoallyl alcohol 4a (see for example, S. Silver, Eur. J. Org. Chem. 2005, 1058). Oxidation of the double bond in 4a affords acid 4b (see for example, R. Almquist, J. Med. Chem. 1985, 28, 1062). Curtis rearrangement of 4b affords the intermediate isocyanate which undergoes intramolecular cyclization to afford the oxazolidinone 4c. Debenzylation under standard hydrogenation conditions affords acid 4d. Coupling of acid 4d with amine 1b (WO 2007092681) in the presence of a base such as triethylamine and a coupling reagent such as BOP or EDAC and HOBt affords the compounds of the type 4e.

Compounds of the type 5e of the present invention can be synthesized as shown in Scheme 5. Oxidative cleavage of the double bond in 4a using for example ozone gas affords the aldehyde 5a. Reductive amination of 5a (see for example, D. Dube, Tetrahedron Lett. 1999, 40, 2295) affords amine 5b. Cyclization of 5b using a carbonyl source such as carbonyldiimidazole or dimethylcarbonate affords the corresponding spirocyclic oxazolidinone 5c, which upon debenzylation under standard hydrogenation conditions affords acid 5d. Coupling of acid 5d with amine 1b (WO 2007092681) in the presence of a base such as triethylamine and a coupling reagent such as BOP or EDAC and HOBt affords the compounds of the type 5e.

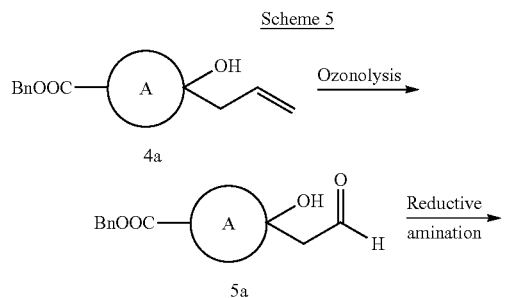

Scheme 5

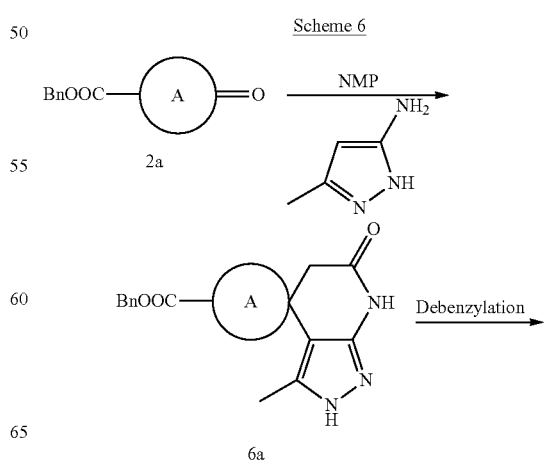

Scheme 6

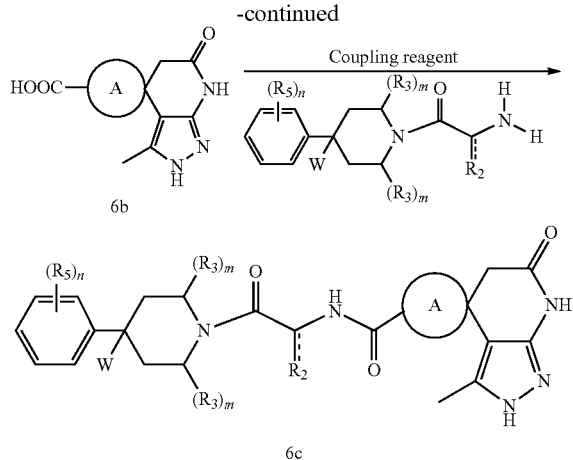

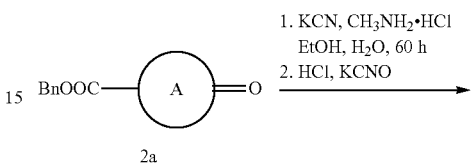

Compounds of the type 6c of the present invention can be synthesized as shown in Scheme 6. Treatment of the keto benzylester 2a with an aminopyrazole using conditions described in (V. Lipson, Chemistry of Heterocyclic Compounds, 2007, 43, 490) affords 6a. Debenzylation of 6a under standard hydrogenation conditions yields acid 6b. Coupling of acid 6b with amine 1b (WO 2007092681) in the presence of a base such as triethylamine and a coupling reagent such as BOP or EDAC and HOBt affords the compounds of the type 6c.

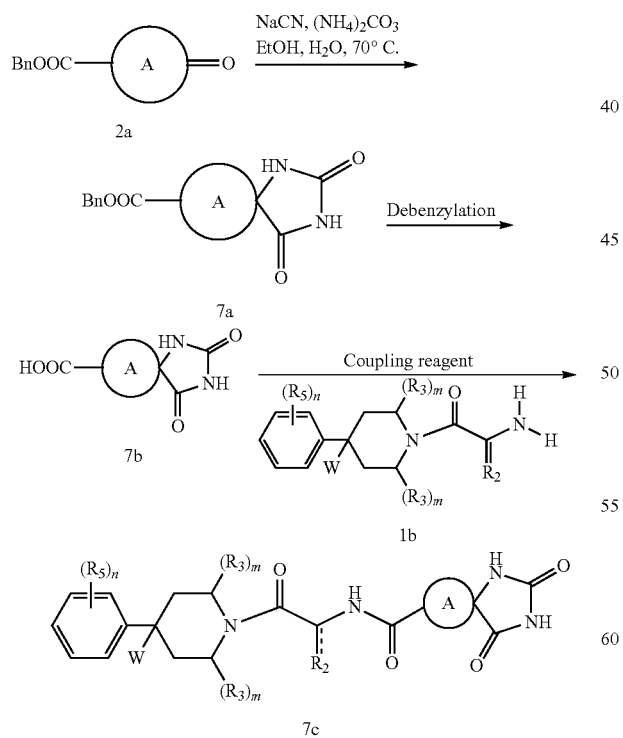

Compounds of the type 7c of the present invention can be synthesized as shown in Scheme 7. Treatment of the ketobenzyl ester 2a using sodium cyanide and ammonium carbonate (see for example, P. Kiviranta, Bioorg. Med. Chem. Lett. 2007, 17, 2448) affords the hydantoin 7a. Debenzylation of 7a under standard hydrogenation conditions yields acid 7b. Coupling of acid 7b with amine 1b (WO 2007092681) in the presence of a base such as triethylamine and a coupling reagent such as BOP or EDAC and HOBt affords the compounds of the type of 7c.

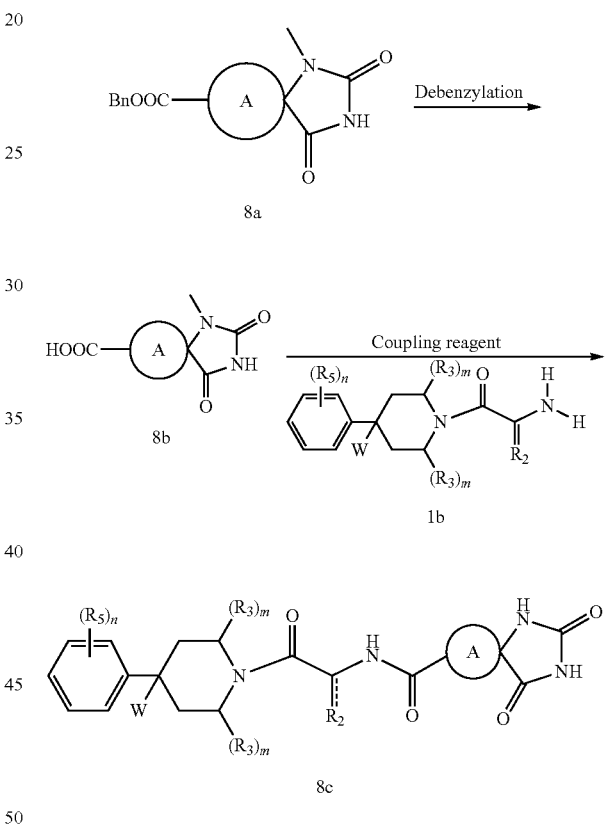

Compounds of the type 8c of the present invention can be synthesized as shown in Scheme 8. Treatment of the ketobenzyl ester 2a using a cyanide source such as sodium or potassium cyanide and an amine such as methyl amine under modified Strecker's conditions affords the intermediate aminonitrile, which upon cyclization and hydrolysis with potassium cyanate affords the hydantoin 8a (see for example, G. Carrera, Journal of Heterocyclic Chemistry, 1992, 29, 847). Debenzylation of 8a under standard hydrogenation conditions yields acid 8b. Coupling of acid 8b with amine 1b (WO 2007092681) in the presence of a base such as triethylamine and a coupling reagent such as BOP or EDAC and HOBt affords the compounds of the type of 8c.

Scheme 9

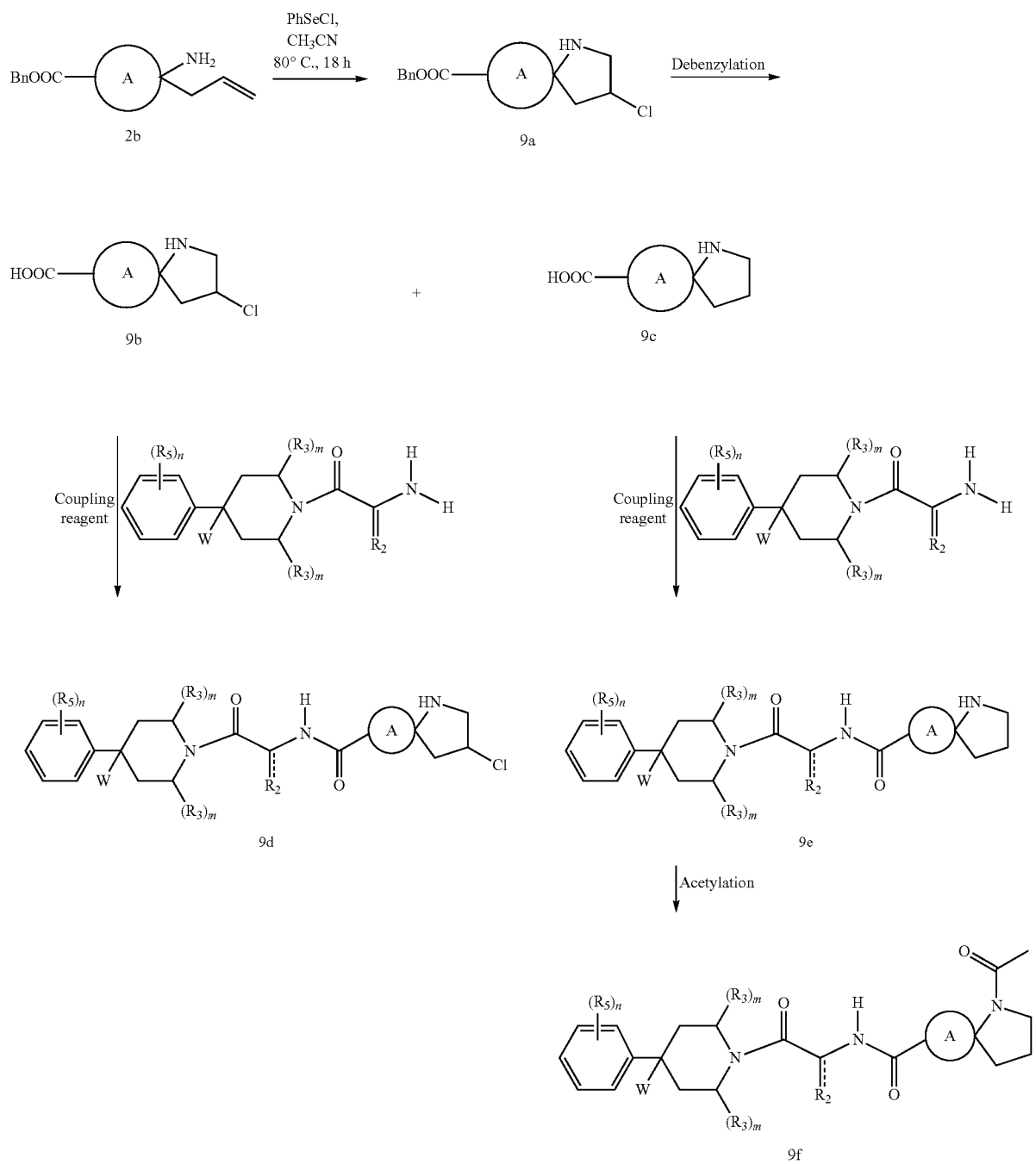

Compounds of the type 9d, 9e and 9f of the present invention can be synthesized as shown in Scheme 9. Phenyl selenium chloride induced cyclization of 2b affords 9a. Debenzylation of 9a under standard hydrogenation conditions can either exclusively afford the acid 9c and or the chloro acid 9b. Coupling of acid 9b and 9c individually with amine 1b (WO 2007092681) in the presence of a base such as triethylamine and a coupling reagent such as BOP or EDAC and HOBt affords the compounds of the type 9d and 9e. Acetylation of 9e under standard acetylation conditions yields compounds of the type 9f.

EXAMPLES

Abbreviations used in the Examples are defined as "2×" for twice, "3×" for thrice, "° C." for degrees Celsius, "g" for gram or grams, "mmol" for millimolar, "mL" for milliliter or milliliters, "M" for molar, "min" for minute or minutes, "mg" for milligram or milligrams, "h" for hour or hours, "LC" for liquid chromatography, "HPLC" for high performance liquid chromatography, "MS" for mass spectroscopy, "RT" for room temperature, "THF" for tetrahydrofuran, "Et₂O" for diethyl ether, "EtOAc" for ethyl acetate, "Na₂SO₄" for

Example 1

(2R)-N-((R)-1-((S)-4-(4-chlorophenyl)-4-hydroxy-3,3-dimethylpiperidin-1-yl)-3-methyl-1-oxobutan-2-yl)-7-oxo-8-oxa-6-azaspiro[4.5]decane-2-carboxamide

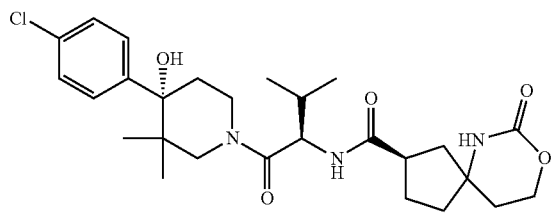 [SMILES: CC(C)[C@@H](NC(=O)[C@@H]1CCC2(CCOC(=O)N2)C1)C(=O)N1CC[C@](O)(c2ccc(Cl)cc2)C(C)(C)C1]

Step A: (R)-N-((R)-1-((S)-4-(4-chlorophenyl)-4-hydroxy-3,3-dimethylpiperidin-1-yl)-3-methyl-1-oxobutan-2-yl)-3-oxocyclopentanecarboxamide

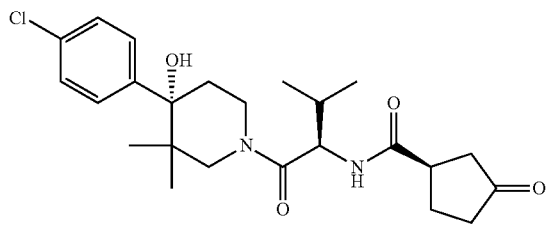 [SMILES: CC(C)[C@@H](NC(=O)[C@@H]1CCC(=O)C1)C(=O)N1CC[C@](O)(c2ccc(Cl)cc2)C(C)(C)C1]

To a solution of (R)-2-amino-1-((S)-4-(4-chlorophenyl)-4-hydroxy-3,3-dimethylpiperidin-1-yl)-3-methylbutan-1-one, hydrogen chloride salt (WO 2007092681, 300 mg, 0.799 mmol) in THF (2 mL) was added (R)-3-oxocyclopentanecarboxylic acid (WO 2007092681, 102 mg, 0.799 mmol), triethylamine (0.223 mL, 1.599 mmol) and BOP (354 mg, 0.799 mmol) at room temperature. The resulting mixture was stirred at room temperature for 3 hours. The reaction mixture was concentrated and partitioned between ethyl acetate (15 mL) and 1N hydrogen chloride (1 mL). The organic layer was washed with water (3 mL), brine (2 mL), dried over anhydrous $Na_2SO_4$, concentrated under reduced pressure and the residue was subjected to preparative HPLC (Shimadzu VP-ODS 20×100 mm, 8 min. gradient, Solvent A: 10% MeOH, 90% $H_2O$, 0.1% TFA; Solvent B: 90% MeOH, 10% $H_2O$, 0.1% TFA; wavelength: 220 nM). The desired fractions were concentrated and freeze dried to yield (R)-N-((R)-1-((S)-4-(4-chlorophenyl)-4-hydroxy-3,3-dimethylpiperidin-1-yl)-3-methyl-1-oxobutan-2-yl)-3-oxocyclopentanecarboxamide (300 mg, 0.668 mmol, 84% yield) as a solid. MS (ESI$^+$) m/z 449 M$^+$

Step B: (1R)-3-allyl-3-amino-N-((R)-1-((S)-4-(4-chlorophenyl)-4-hydroxy-3,3-dimethylpiperidin-1-yl)-3-methyl-1-oxobutan-2-yl)cyclopentanecarboxamide

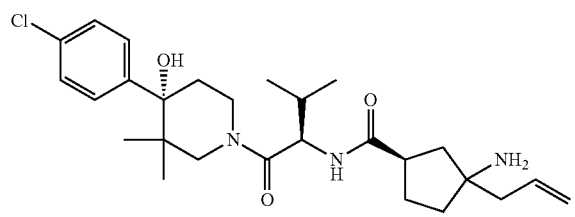 [SMILES: C=CCC1(N)CC[C@@H](C(=O)N[C@@H](C(=O)N2CC[C@](O)(c3ccc(Cl)cc3)C(C)(C)C2)C(C)C)C1]

To (R)-N-((R)-1-((S)-4-(4-chlorophenyl)-4-hydroxy-3,3-dimethylpiperidin-1-yl)-3-methyl-1-oxobutan-2-yl)-3-oxocyclopentanecarboxamide (from step A, 300 mg, 0.668 mmol) was added ammonia (954 µL, 6.68 mmol) followed by 2-allyl-4,4,5,5-tetramethyl-1,3,2-dioxaborolane (168 mg, 1.0 mmol) at room temperature. The resulting mixture was stirred at room temperature for 16 hours. The reaction mixture was concentrated under reduced pressure and the residue was subjected to preparative HPLC (Shimadzu VP-ODS 20×100 mm, 8 min. gradient, Solvent A: 10% MeOH, 90% $H_2O$, 0.1% TFA; Solvent B: 90% MeOH, 10% $H_2O$, 0.1% TFA; wavelength: 220 nM). The desired fractions were collected, concentrated and partitioned between ethyl acetate (20 mL) and sat. aqueous sodium bicarbonate (10 mL). The organic layer was dried over anhydrous $Na_2SO_4$ and concentrated under reduced pressure to yield (1R)-3-allyl-3-amino-N-((R)-1-((S)-4-(4-chlorophenyl)-4-hydroxy-3,3-dimethylpiperidin-1-yl)-3-methyl-1-oxobutan-2-yl)cyclopentanecarboxamide (150 mg, 0.30 mmol, 45.8% yield) as a solid. MS (ESI$^+$) m/z 490 M$^+$

Step C: tert-butyl (3R)-1-allyl-3-((R)-1-((S)-4-(4-chlorophenyl)-4-hydroxy-3,3-dimethylpiperidin-1-yl)-3-methyl-1-oxobutan-2-ylcarbamoyl)cyclopentyl carbamate

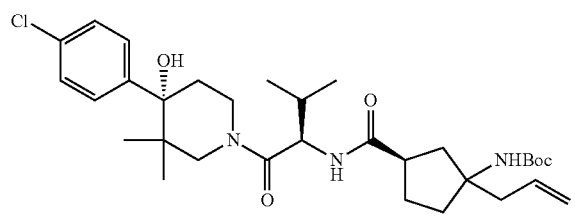 [SMILES: C=CCC1(NC(=O)OC(C)(C)C)CC[C@@H](C(=O)N[C@@H](C(=O)N2CC[C@](O)(c3ccc(Cl)cc3)C(C)(C)C2)C(C)C)C1]

To a solution of (1R)-3-allyl-3-amino-N-((R)-1-((S)-4-(4-chlorophenyl)-4-hydroxy-3,3-dimethylpiperidin-1-yl)-3-methyl-1-oxobutan-2-yl)cyclopentanecarboxamide (from step B, 60 mg, 0.122 mmol) in dichloromethane (2 mL) was added di-tert-butyl dicarbonate (32 mg, 0.147 mmol) and triethylamine (0.034 mL, 0.245 mmol). The resulting mixture was stirred at room temperature for 16 hours. The reaction mixture was diluted with dichloromethane (10 mL) and sequentially washed with 1N hydrogen chloride (1 mL), water (5 mL), brine (5 ML), dried over $Na_2SO_4$ and concentrated to yield tert-butyl (3R)-1-allyl-3-((R)-1-((S)-4-(4-chlorophenyl)-4-hydroxy-3,3-dimethylpiperidin-1-yl)-3-methyl-1-oxobutan-2-ylcarbamoyl)cyclopentylcarbamate (70 mg, 0.119 mmol, 97% yield) as a clear oil. MS (ESI+) m/z 590 M+

Step D: tert-butyl (3R)-3-((R)-1-((S)-4-(4-chlorophenyl)-4-hydroxy-3,3-dimethylpiperidin-1-yl)-3-methyl-1-oxobutan-2-ylcarbamoyl)-1-(2-oxoethyl)cyclopentylcarbamate

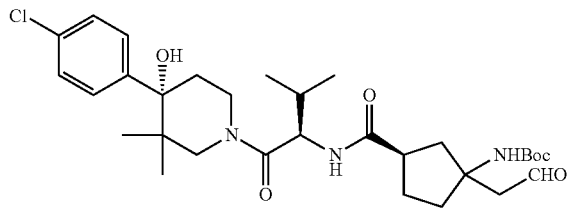 [SMILES: CC(C)[C@@H](NC(=O)[C@@H]1CCC(CC=O)(NC(=O)OC(C)(C)C)C1)C(=O)N1CC[C@](O)(c2ccc(Cl)cc2)C(C)(C)C1]

Tert-butyl (3R)-1-allyl-3-((R)-1-((S)-4-(4-chlorophenyl)-4-hydroxy-3,3-dimethylpiperidin-1-yl)-3-methyl-1-oxobutan-2-ylcarbamoyl)cyclopentylcarbamate (from step C, 70 mg, 0.119 mmol) was dissolved in dichloromethane (5 mL) and ozonized at −78° C. until the blue color persists. The reaction mixture was purged with nitrogen gas until the blue color disappeared. To the reaction mixture was added triethylamine (0.5 mL) and the contents allowed to warm up to room temperature and stirred at room temperature for an additional 1 hour. The reaction mixture was passed through a 4g silica gel cartridge (eluted with ethyl acetate) and the eluate was concentrated to yield t-butyl (3R)-3-((R)-1-((S)-4-(4-chlorophenyl)-4-hydroxy-3,3-dimethylpiperidin-1-yl)-3-methyl-1-oxobutan-2-ylcarbamoyl)-1-(2-oxoethyl)cyclopentylcarbamate (60 mg, 0.101 mmol, 85% yield) as an oil. MS (ESI+) m/z 592 M+

Step E: tert-butyl (3R)-3-((R)-1-((S)-4-(4-chlorophenyl)-4-hydroxy-3,3-dimethylpiperidin-1-yl)-3-methyl-1-oxobutan-2-ylcarbamoyl)-1-(2-hydroxyethyl)cyclopentylcarbamate

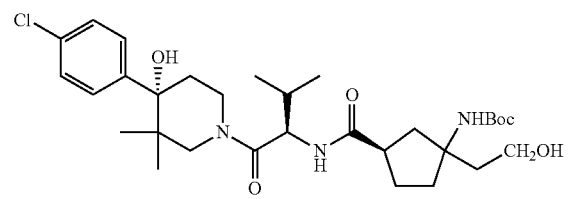 [SMILES: CC(C)[C@@H](NC(=O)[C@@H]1CCC(CCO)(NC(=O)OC(C)(C)C)C1)C(=O)N1CC[C@](O)(c2ccc(Cl)cc2)C(C)(C)C1]

To a solution of tert-butyl (3R)-3-((R)-1-((S)-4-(4-chlorophenyl)-4-hydroxy-3,3-dimethylpiperidin-1-yl)-3-methyl-1-oxobutan-2-ylcarbamoyl)-1-(2-oxoethyl)cyclopentylcarbamate (from step D, 60 mg, 0.101 mmol) in MeOH (2 mL) at −78° C. was added NaBH4 (7.67 mg, 0.203 mmol). The resulting mixture was stirred at −78° C. for 1 hour. The solvent was removed under reduced pressure and to the residue was added ethyl acetate (10 mL). The resulting mixture was washed with water (2 mL), brine (2 mL), dried over Na2SO4 and concentrated to yield t-butyl (3R)-3-((R)-1-((S)-4-(4-chlorophenyl)-4-hydroxy-3,3-dimethylpiperidin-1-yl)-3-methyl-1-oxobutan-2-ylcarbamoyl)-1-(2-hydroxyethyl)cyclopentylcarbamate (58 mg, 0.098 mmol, 96% yield) as a solid. MS (ESI+) m/z 594 M+

Step F: (1R)-3-amino-N-((R)-1-((S)-4-(4-chlorophenyl)-4-hydroxy-3,3-dimethylpiperidin-1-yl)-3-methyl-1-oxobutan-2-yl)-3-(2-hydroxyethyl)cyclopentanecarboxamide

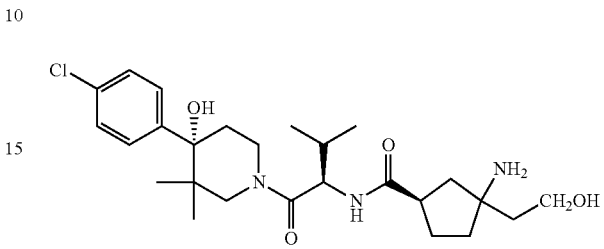

To t-butyl (3R)-3-((R)-1-((S)-4-(4-chlorophenyl)-4-hydroxy-3,3-dimethylpiperidin-1-yl)-3-methyl-1-oxobutan-2-ylcarbamoyl)-1-(2-hydroxyethyl)cyclopentylcarbamate (58 mg, 0.098 mmol) was added hydrogen chloride (4M in dioxane, 0.5 mL). The resulting mixture was stirred at room temperature for 1 hour. The reaction mixture was concentrated to yield (1R)-3-amino-N -((R)-1-((S)-4-(4-chlorophenyl)-4-hydroxy-3,3-dimethylpiperidin-1-yl)-3-methyl-1-oxobutan-2-yl)-3-(2-hydroxyethyl)cyclopentanecarboxamide, hydrogen chloride salt (50 mg, 0.094 mmol, 97% yield) as an oil. It was used as such for the next step without further purification. MS (ESI+) m/z 494 M+

Step G: (2R)-N-((R)-1-((S)-4-(4-chlorophenyl)-4-hydroxy-3,3-dimethylpiperidin-1-yl)-3-methyl-1-oxobutan-2-yl)-7-oxo-8-oxa-6-azaspiro[4.5]decane-2-carboxamide

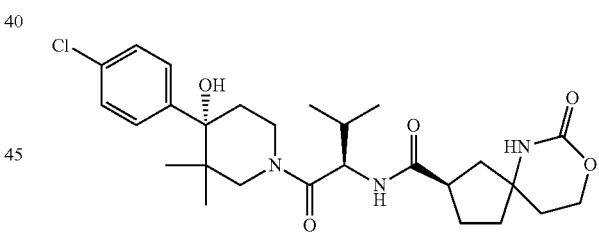

To a solution of (1R)-3-amino-N-((R)-1-((S)-4-(4-chlorophenyl)-4-hydroxy-3,3-dimethylpiperidin-1-yl)-3-methyl-1-oxobutan-2-yl)-3-(2-hydroxyethyl)cyclopentanecarboxamide (from step F, 30 mg, 0.061 mmol) in THF (1 mL) was added carbonyl diimidazole (14.77 mg, 0.091 mmol) and triethylamine (0.021 mL, 0.152 mmol). The resulting mixture was stirred at room temperature for 4 hours. The reaction mixture was concentrated and subjected preparative HPLC (Shimadzu VP-ODS 20×100 mm, 8 min. gradient, Solvent A: 10% MeOH, 90% H2O, 0.1% TFA; Solvent B: 90% MeOH, 10% H2O, 0.1% TFA; wavelength: 220 nM) to yield the desired product as a diastereomer mixture. The diastereomer mixture was subjected to chiral preparative HPLC (Column: ChiralPak ASH, 250×3 cm, 5 µm; Flow rate: 120 mL/min; Mobile Phase: CO2/MeOH=80/20; Inj. Vol.=2.0 mL, Wavelength=220 nM; isomer 1, retention time=5.75 min; isomer 2, retention time=9.10 min) to yield the individual diastereomers (2 mg for each isomer, 3.85 µmol, 6.33% yield) as a solid.

Isomer 1: MS (ESI⁺)=520 M⁺; Purity: >95%; 1H NMR (500 MHz, CHLOROFORM-d) [rotamers, Integration values are assigned based on a 1:1 inseparable mixture of a and b rotamers for a total of 74 protons, excluding the OH proton] δ ppm 0.77 (s, 6 H) 0.81-0.99 (m, 12 H) 1.05 (d, J=6.87 Hz, 3 H) 1.41-2.24 (m, 27 H) 2.53-2.72 (m, J=17.91, 13.52, 13.52, 4.81 Hz, 2 H) 2.76-2.95 (m, J=9.83, 9.59, 9.59, 4.54 Hz, 1 H) 3.18 (td, J=13.06, 2.75 Hz, 1 H) 3.38 (dd, J=13.20, 1.37 Hz, 1 H) 3.61 (d, J=13.47 Hz, 1 H) 3.64-3.71 (m, 1 H) 3.94 (dd, J=14.16, 2.89 Hz, 1 H) 4.11 (dd, J=13.20, 1.65 Hz, 1 H) 4.21-4.37 (m, 2 H) 4.65 (dd, J=12.37, 4.12 Hz, 1 H) 4.96 (td, J=9.14, 5.64 Hz, 2 H) 6.47 (d, J=8.80 Hz, 1 H) 6.55 (d, J=8.80 Hz, 1 H) 6.99 (s, 1 H) 7.13 (s, 1 H) 7.29-7.50 (m, 8 H); RP-HPLC: Retention time=3.1 min (YMC S5 ODS 4.6×50 mm; 4 min gradient, run time 8 min, solvent A: 10% MeOH, 90% H₂O, 0.2% H₃PO₄; Solvent B: 90% MeOH, 10% H₂O, 0.2% H₃PO₄);

Isomer 2: MS (ESI⁺)=520 M⁺; Purity: >95%; RP-HPLC: Retention time=3.1 min (YMC S5 ODS 4.6×50 mm; 4 min gradient, run time 8 min, solvent A: 10% MeOH, 90% H₂O, 0.2% H₃PO₄; Solvent B: 90% MeOH, 10% H₂O, 0.2% H₃PO₄.

Example 2

(2R)-N-((R)-1-((S)-4-(4-chlorophenyl)-4-hydroxy-3,3-dimethylpiperidin-1-yl)-3-methyl-1-oxobutan-2-yl)-7-oxo-6,8-diazaspiro[4.5]decane-2-carboxamide

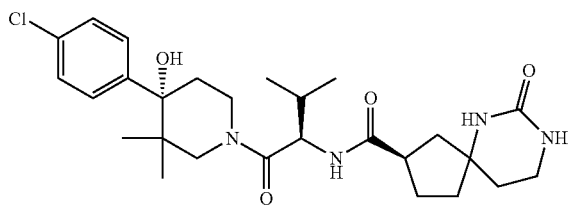 [SMILES: CC(C)[C@@H](NC(=O)[C@@H]1CCC2(CCNC(=O)N2)C1)C(=O)N1CC[C@](O)(c2ccc(Cl)cc2)C(C)(C)C1]

Step A: (1R)-benzyl 3-allyl-3-aminocyclopentanecarboxylate

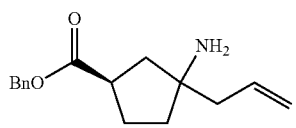 [SMILES: C=CCC1(N)CC[C@@H](C(=O)OCc2ccccc2)C1]

To a solution of (R)-benzyl 3-oxocyclopentanecarboxylate (WO 2007092681, 1 g, 4.58 mmol) in methanol (5 mL) was added 2-allyl-4,4,5,5-tetramethyl-1,3,2-dioxaborolane (1.155 g, 6.87 mmol) and ammonia (7N solution in MeOH, 8 mL). The resulting mixture was stirred at room temperature for 16 hours. The reaction mixture was concentrated and the residue was subjected to preparative HPLC (Shimadzu VP-ODS 20×100 mm, 8 min. gradient, Solvent A: 10% MeOH, 90% H₂O, 0.1% TFA; Solvent B: 90% MeOH, 10% H₂O, 0.1% TFA; wavelength: 220 nM). The desired fractions were collected, concentrated and partitioned between ethyl acetate (20 mL) and saturated aqueous sodium bicarbonate solution (10 mL). The organic layer was dried over anhydrous Na₂SO₄ and concentrated under reduced pressure to yield (1R)-benzyl 3-allyl-3-aminocyclopentanecarboxylate (616 mg, 2.38 mmol, 52% yield). MS (ESI⁺) m/z 260 (M+H)⁺

Step B: (1R)-benzyl 3-allyl-3-(tert-butoxycarbonylamino)cyclo pentanecarboxylate

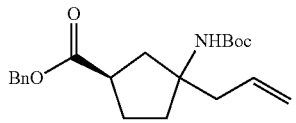 [SMILES: C=CCC1(NC(=O)OC(C)(C)C)CC[C@@H](C(=O)OCc2ccccc2)C1]

To a solution of (1R)-benzyl 3-allyl-3-aminocyclopentanecarboxylate (from step A, 370 mg, 1.427 mmol) in dichloromethane (5 mL) was added triethylamine (0.398 mL, 2.85 mmol) and di-tert-butyl dicarbonate (374 mg, 1.712 mmol). The resulting mixture was stirred at room temperature for 16 hours. To the reaction mixture was added dichloromethane (20 mL) and the resulting mixture was washed with 1N hydrogen chloride (5 mL), water (5 ml), brine (5 mL), dried over Na₂SO₄ and concentrated to yield (1R)-benzyl 3-allyl-3-(tert-butoxycarbonylamino)cyclopentanecarboxylate (480 mg, 1.335 mmol, 94% yield) as an oil. MS (ESI⁺) m/z 382 (M+Na)⁺

Step C: (1R)-benzyl 3-(tert-butoxycarbonylamino)-3-(2-oxoethyl)cyclo pentanecarboxylate

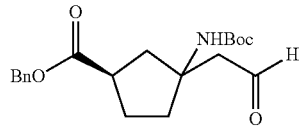 [SMILES: CC(C)(C)OC(=O)NC1(CC=O)CC[C@@H](C(=O)OCc2ccccc2)C1]

(1R)-benzyl 3-allyl-3-(tert-butoxycarbonylamino)cyclopentanecarboxylate (from step B, 100 mg, 0.278 mmol) was dissolved in dichloromethane (3 mL) and ozonized at –78° C. until the blue color persists. The reaction mixture was purged with nitrogen gas until the blue color disappeared. To the reaction mixture was added triethylamine (0.5 mL) and the contents allowed to warm up to room temperature and stirred at room temperature for additional 1 hour. The reaction mixture was passed through a 4 g silica gel cartridge (eluted with ethyl acetate) and the eluate was concentrated to yield (1R)-benzyl 3-(tert-butoxycarbonylamino)-3-(2-oxoethyl)cyclopentanecarboxylate (80 mg, 0.221 mmol, 80% yield) as an oil. It was used as such for the next step without further purification.

Step D: (1R)-benzyl 3-amino-3-(2-aminoethyl)cyclopentanecarboxylate

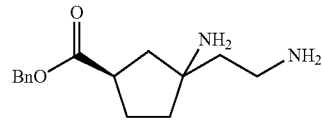 [SMILES: NCCC1(N)CC[C@@H](C(=O)OCc2ccccc2)C1]

To a solution of (1R)-benzyl 3-(tert-butoxycarbonylamino)-3-(2-oxoethyl)cyclopentanecarboxylate (from step C, 80 mg, 0.221 mmol) in acetonitrile (2 mL) was added tert-butyl carbamate (78 mg, 0.664 mmol), triethylsilane (77 mg, 0.664 mmol) and trifluoroacetic acid (1.705 μL, 0.022 mmol). The resulting mixture was stirred at room temperature for 4 hours. The reaction mixture was concentrated under reduced pressure to yield an oil which was treated with hydrogen chloride (4M in dioxane, 1 mL) at room temperature. After the reaction was stirred at room temperature for 1 hour, the reaction mixture was concentrated and subjected to preparative HPLC(Shimadzu VP-ODS 20×100 mm, 8 min. gradient, Solvent A: 10% MeOH, 90% H$_2$O, 0.1% TFA; Solvent B: 90% MeOH, 10% H$_2$O, 0.1% TFA; wavelength: 220 nM). The desired fractions were concentrated under reduced pressure to yield (1R)-benzyl 3-amino-3-(2-aminoethyl)cyclopentanecarboxylate, 2 trifluoroacetic acid salt (56.1 mg, 0.114 mmol, 51.7% yield in 2 steps) as an oil. MS (ESI$^+$) m/z 263 (M+H)$^+$ Step E: (2R)-benzyl 7-oxo-6,8-diazaspiro[4.5]decane-2-carboxylate

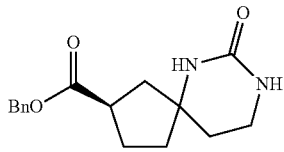 [SMILES: O=C1NCCC2(CC[C@@H](C(=O)OCc3ccccc3)C2)N1]

To a solution of (1R)-benzyl 3-amino-3-(2-aminoethyl) cyclopentanecarboxylate (from step D, 30 mg, 0.114 mmol) in toluene (2 mL) was added triethylamine (0.048 mL, 0.343 mmol) and 1,1'-Carbonyldiimidazole (37.1 mg, 0.229 mmol). The resulting mixture was stirred at 80° C. for 2 hours. To the reaction mixture was added ethyl acetate (10 mL) and the resulting mixture was washed with 1N hydrogen chloride (1 mL), water (2 mL), brine (2 mL), dried over Na$_2$SO$_4$ and concentrated under reduced pressure to yield (2R)-benzyl 7-oxo-6,8-diazaspiro[4.5]decane-2-carboxylate (20 mg, 0.069 mmol, 60.7% yield) as an oil. It was used as such for the subsequent step without further purification. MS (ESI$^+$) m/z 288 M$^+$ Step F: (2R)-7-oxo-6,8-diazaspiro[4.5]decane-2-carboxylic acid

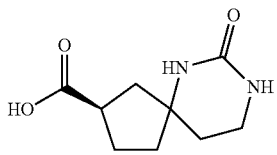 [SMILES: O=C1NCCC2(CC[C@@H](C(=O)O)C2)N1]

To a solution of (2R)-benzyl 7-oxo-6,8-diazaspiro[4.5]decane-2-carboxylate (from step E, 20 mg, 0.069 mmol) in methanol (2 mL) was added palladium (Pd/C, 10% wt., 7.38 mg, 6.94 mmol). The resulting mixture was stirred under a hydrogen balloon for 30 min. The reaction mixture was filtered. The filtrate was concentrated under reduced pressure to yield (2R)-7-oxo-6,8-diazaspiro[4.5]decane-2-carboxylic acid (10 mg, 0.050 mmol, 72.7% yield) as an oil. It was used as such for the next step without further purification. MS m/z 199 (M+H)$^+$ Step G: (2R)-N-((R)-1-((S)-4-(4-chlorophenyl)-4-hydroxy-3,3-dimethylpiperidin-1-yl)-3-methyl-1-oxobutan-2-yl)-7-oxo-6,8-diazaspiro[4.5]decane-2-carboxamide

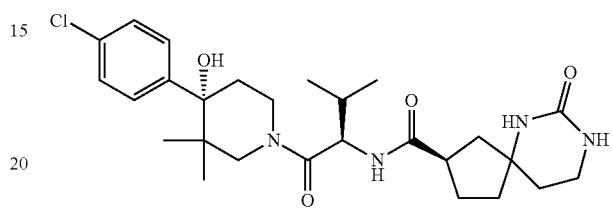

To a solution of (2R)-7-oxo-6,8-diazaspiro[4.5]decane-2-carboxylic acid (from step F, 10 mg, 0.050 mmol) in THF (1 mL) was added (R)-2-amino-1-((S)-4-(4-chlorophenyl)-4-hydroxy-3,3-dimethylpiperidin-1-yl)-3-methylbutan-1-one, hydrogen chloride salt (34.2 mg, 0.091 mmol), triethylamine (7.03 μL, 0.050 mmol) and BOP (22.31 mg, 0.050 mmol). The resulting mixture was stirred at room temperature for 2 hours. The reaction mixture was subjected to preparative HPLC(Shimadzu VP-ODS 20×100 mm, 8 min. gradient, Solvent A: 10% MeOH, 90% H$_2$O, 0.1% TFA; Solvent B: 90% MeOH, 10% H$_2$O, 0.1% TFA; wavelength: 220 nM). The desired fractions were concentrated under reduced pressure and freeze dried to yield (2R)-N-((R)-1-((S)-4-(4-chlorophenyl)-4-hydroxy-3,3-dimethylpiperidin-1-yl)-3-methyl-1-oxobutan-2-yl)-7-oxo-6,8-diazaspiro[4.5]decane-2-carboxamide (4 mg, solid, 7.71 mmol, 15.27% yield) as a mixture of diasteromers. RP-HPLC: Retention time=3.19 min (YMC S5 ODS 4.6×50 mm; 4 min gradient, run time 8 min, solvent A: 10% MeOH, 90% H$_2$O, 0.2% H$_3$PO$_4$; Solvent B: 90% MeOH, 10% H2O, 0.2% H$_3$PO$_4$); Purity: >95%; MS (ESI$^+$) m/z 519 M$^+$ Example 3

N-((R)-1-((S)-4-(4-chlorophenyl)-4-hydroxy-3,3-dimethylpiperidin-1-yl)-3-methyl-1-oxobutan-2-yl)-7-oxo-6-oxa-8-azaspiro[4.5]decane-1-carboxamide

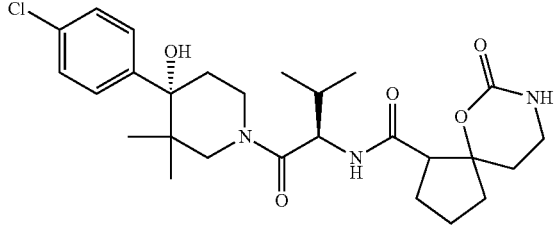 [SMILES: CC(C)[C@@H](NC(=O)C1CCCC12CCNC(=O)O2)C(=O)N1CC[C@](O)(c2ccc(Cl)cc2)C(C)(C)C1]

Step A: benzyl 2-oxocyclopentanecarboxylate

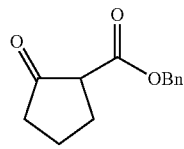 [SMILES: O=C1CCCC1C(=O)OCc1ccccc1]

To ethyl 2-oxocyclopentanecarboxylate (4 g, 25.6 mmol) was added benzyl alcohol (3.6 g, 33.3 mmol) and the resulting mixture was heated to 175° C. for 1 hour. The reaction mixture was concentrated under reduced pressure using a high vacuum pump to yield benzyl 2-oxocyclopentanecarboxylate (5.2 g, 23.84 mmol, 93% yield) as an oil. This compound was used for the next step without further purification.

Step B: Benzyl 2-allyl-2-hydroxycyclopentanecarboxylate (homochiral)

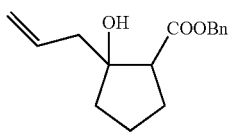

To a solution of benzyl 2-oxocyclopentanecarboxylate (from step A, 5 g, 22.91 mmol) in a mixture of methanol (20 ml) and water (60.00 ml) was added 3-bromoprop-1-ene (8.31 g, 68.7 mmol) and indium (1.081 ml, 68.7 mmol). The resulting mixture was stirred at room temperature for 16 hours. The reaction mixture was concentrated and to the residue was added 1N hydrogen chloride (15 mL) and stirred at room temperature for 5 min. The reaction mixture was partitioned between ethyl acetate (30 mL) and water (4 mL). The ethyl acetate layer is washed with brine (4 mL), dried over anhydrous $Na_2SO_4$ and concentrated under the reduced pressure. The residue was subjected to preparative HPLC (Shimadzu VP-ODS 20×100 mm, 8 min. gradient, Solvent A: 10% MeOH, 90% $H_2O$, 0.1% TFA; Solvent B: 90% MeOH, 10% $H_2O$, 0.1% TFA; wavelength: 220 nM). The desired fractions were collected, concentrated under reduced pressure to yield the desired product as a diastereomer mixture. The diastereomer mixture was subjected to chiral preparative HPLC to yield four individual isomers. The fractions corresponding to the second isomer was concentrated and freeze dried to yield a solid (800 mg, 3.08 mmol, 13.4% yield). Chiral HPLC method: Column. ChiralPak AD-H, 250×3 cm, 5 µm; Flow rate: 130 mL/min; Mobile Phase: $CO_2$/MeOH=70/30; Inj. Vol.=0.7 mL, Wavelength=220 nM,: Retention time=3.18 min. MS ($ESI^+$)=283 (M+Na)$^+$

Step C: Benzyl 2-hydroxy-2-(2-oxoethyl)cyclopentanecarboxylate ((homochiral)

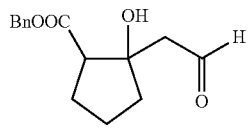

Benzyl 2-allyl-2-hydroxycyclopentanecarboxylate (from step B, 150 mg, 0.576 mmol) was dissolved in dichloromethane (5 mL) and ozonized at −78° C. until the blue color persists. The reaction mixture was purged with nitrogen gas until the blue color disappeared. To the reaction mixture was added triethylamine (0.5 mL) and the contents allowed to warm up to room temperature and stirred at room temperature for an additional 1 hour. The reaction mixture was passed through a 4 g silica gel cartridge (eluted with ethyl acetate) and the eluate was concentrated to yield benzyl 2-hydroxy-2-(2-oxoethyl)cyclopentanecarboxylate (120 mg, 0.457 mmol, 79% yield) as an oil. It was used as such for the next step without further purification.

Step D: Benzyl 2-(2-(tert-butoxycarbonylamino)ethyl)-2-hydroxycyclopentanecarboxylate (homochiral)

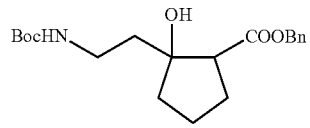

To a solution of benzyl 2-hydroxy-2-(2-oxoethyl)cyclopentanecarboxylate (from step C, 120 mg, 0.457 mmol) in acetonitrile (2 mL) was added tert-butyl carbamate (214 mg, 1.830 mmol), triethylsilane (213 mg, 1.830 mmol) and trifluoroacetic acid (0.070 mL, 0.915 mmol). The resulting mixture was stirred at room temperature for 3 hours. The reaction mixture was concentrated and subjected to preparative HPLC (Shimadzu VP-ODS 20×100 mm, 8 min. gradient, Solvent A: 10% MeOH, 90% $H_2O$, 0.1% TFA; Solvent B: 90% MeOH, 10% $H_2O$, 0.1% TFA; wavelength: 220 nM). The desired fractions were concentrated and freeze dried to yield benzyl 2-(2-(tert-butoxycarbonylamino)ethyl)-2-hydroxycyclopentanecarboxylate (70 mg, 0.193 mmol, 42.1% yield) as a solid. MS ($ESI^+$)=386 (M+Na)$^+$

Step E: 2-(2-(t-butoxycarbonylamino)ethyl)-2-hydroxycyclopentanecarboxylic acid (homochiral)

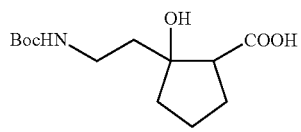 [SMILES: CC(C)(C)OC(=O)NCCC1(O)CCCC1C(=O)O]

To a solution of benzyl 2-(2-(t-butoxycarbonylamino)ethyl)-2-hydroxycyclopentanecarboxylate (from step D, 70 mg, 0.193 mmol) in MeOH (3 mL) was added palladium (10% wt Pd/C, 20.50 mg, 0.019 mmol). The resulting mixture was stirred under a hydrogen balloon for 30 min. The reaction mixture was filtered. The filtrate was concentrated under reduced pressure to yield 2-(2-(tert-butoxycarbonylamino)ethyl)-2-hydroxycyclopentanecarboxylic acid (50 mg, 0.183 mmol, 95% yield) as an oil. MS=273 (M+H)⁺

Step F: t-butyl 2-(2-((R)-1-((S)-4-(4-chlorophenyl)-4-hydroxy-3,3-dimethylpiperidin-1-yl)-3-methyl-1-oxobutan-2-ylcarbamoyl)-1-hydroxycyclopentyl)ethylcarbamate

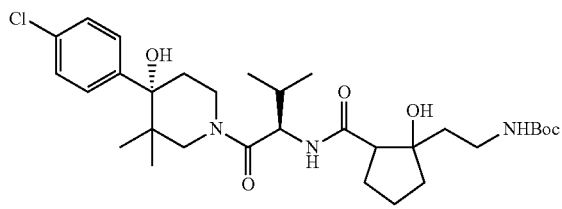 [SMILES: CC(C)[C@@H](NC(=O)C1CCCC1(O)CCNC(=O)OC(C)(C)C)C(=O)N1CC[C@](O)(c2ccc(Cl)cc2)C(C)(C)C1]

To a solution of (R)-2-amino-1-((S)-4-(4-chlorophenyl)-4-hydroxy-3,3-dimethylpiperidin-1-yl)-3-methylbutan-1-one, hydrogen chloride salt (68.7 mg, 0.183 mmol) in THF (2 mL) was added 2-(2-(t-butoxycarbonylamino)ethyl)-2-hydroxycyclopentanecarboxylic acid (from step E, 50 mg, 0.183 mmol), triethylamine (0.051 mL, 0.366 mmol) and BOP (81 mg, 0.183 mmol). The resulting mixture was stirred at room temperature for 16 hours. The solvent was removed under reduced pressure. To the residue was added ethyl acetate (20 mL) and the resulting mixture was washed with water (5 mL), brine (5 mL), dried over anhydrous Na₂SO₄ and concentrated under reduced pressure to yield tert-butyl 2-(2-((R)-1-((S)-4-(4-chlorophenyl)-4-hydroxy-3,3-dimethylpiperidin-1-yl)-3-methyl-1-oxobutan-2-ylcarbamoyl)-1-hydroxycyclopentyl)ethylcarbamate as an oil (100 mg, 0.168 mmol, 92% yield). It was used as such for the next step without further purification. MS (ESI⁺)=494 (M-Boc)⁺

Step G: 2-(2-aminoethyl)-N-((R)-1-((S)-4-(4-chlorophenyl)-4-hydroxy-3,3-dimethylpiperidin-1-yl)-3-methyl-1-oxobutan-2-yl)-2-hydroxycyclopentanecarboxamide

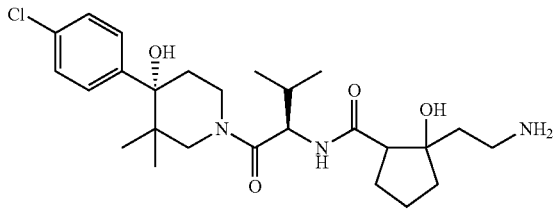 [SMILES: CC(C)[C@@H](NC(=O)C1CCCC1(O)CCN)C(=O)N1CC[C@](O)(c2ccc(Cl)cc2)C(C)(C)C1]

To t-butyl 2-(2-((R)-1-((S)-4-(4-chlorophenyl)-4-hydroxy-3,3-dimethylpiperidin-1-yl)-3-methyl-1-oxobutan-2-ylcarbamoyl)-1-hydroxycyclopentyl)ethylcarbamate (from step F, 100 mg, 0.168 mmol) was added hydrogen chloride (4M in dioxane, 0.5 mL). The resulting mixture was stirred at room temperature for 1 hour. The reaction mixture was concentrated and the residue was partitioned between ethyl acetate (10 mL) and saturated aqueous sodium bicarbonate solution (5 mL). The ethyl acetate layer was concentrated under reduced pressure and the residue was subjected to preparative HPLC (Shimadzu VP-ODS 20×100 mm, 8 min. gradient, Solvent A: 10% MeOH, 90% H₂O, 0.1% TFA; Solvent B: 90% MeOH, 10% H₂O, 0.1% TFA; wavelength: 220 nM). The desired fractions were concentrated under reduced pressure and freeze dried to yield 2-(2-aminoethyl)-N-((R)-1-((S)-4-(4-chlorophenyl)-4-hydroxy-3,3-dimethylpiperidin-1-yl)-3-methyl-1-oxobutan-2-yl)-2-hydroxycyclopentanecarboxamide, trifluoroacetic acid salt (60 mg, 0.099 mmol, 58.6% yield) as a solid. MS (ESI⁺)=494 M⁺

Step H: N-((R)-1-((S)-4-(4-chlorophenyl)-4-hydroxy-3,3-dimethylpiperidin-1-yl)-3-methyl-1-oxobutan-2-yl)-7-oxo-6-oxa-8-azaspiro[4.5]decane-1-carboxamide

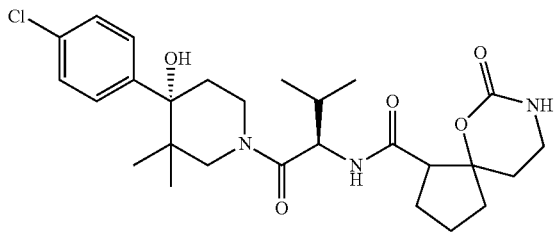 [SMILES: CC(C)[C@@H](NC(=O)C1CCCC12CCNC(=O)O2)C(=O)N1CC[C@](O)(c2ccc(Cl)cc2)C(C)(C)C1]

To a solution of 2-(2-aminoethyl)-N-((R)-1-((S)-4-(4-chlorophenyl)-4-hydroxy-3,3-dimethylpiperidin-1-yl)-3-methyl-1-oxobutan-2-yl)-2-hydroxycyclopentanecarboxamide (from step G, 30 mg, 0.061 mmol) in THF (0.5 mL) was added triethylamine (0.017 mL, 0.121 mmol) and 1,1'-Carbonyldiimidazole (14.77 mg, 0.091 mmol) at room temperature. The resulting mixture was stirred at room temperature for 4 hours. The reaction mixture was subjected to preparative HPLC (Shimadzu VP-ODS 20×100 mm, 8 min. gradient, Solvent A: 10% MeOH, 90% H2O, 0.1% TFA; Solvent B: 90% MeOH, 10% H₂O, 0.1% TFA). The fractions corresponding to each individual diasteromer were collected, concentrated and freeze dried to yield (isomer 1: 8 mg, 0.015 mmol, 25% yield; isomer 2: 6 mg, 0.011 mmol, 19% yield).

Isomer 1: Anal. RP-HPLC: Retention time=2.96 min (YMC S5 ODS 4.6×50 mm; gradient solvent A: 10% MeOH, 90% H₂O, 0.2% H₃PO₄; Solvent B: 90% MeOH, 10% H₂O, 0.2% H₃PO₄). Purity: >95%; MS (ESI⁺)=520 M⁺;

Isomer 2: Anal. RP-HPLC: Retention time=3.07 min (YMC S5 ODS 4.6×50 mm; gradient solvent A: 10% MeOH, 90% H₂O, 0.2% H₃PO₄; Solvent B: 90% MeOH, 10% H₂O, 0.2% H₃PO₄); 1H NMR (400 MHz, CHLOROFORM-d) [rotamers, integration values are assigned based on a 1:1 inseparable mixture of a and b rotamers for a total of 74 protons, excluding the OH proton] δ ppm 0.76 (s, 3 H) 0.80 (s, 3 H) 0.84 (s, 3 H) 0.86 (s, 3 H) 0.88-0.98 (m, 9 H) 1.03 (d, J=6.53 Hz, 3 H) 1.45 (d, J=14.05 Hz, 1 H) 1.60 (d, J=13.55 Hz, 1 H) 1.66-2.31 (m, 13 H) 2.31-2.46 (m, 2 H) 2.55-2.77 (m, 4 H) 3.05-3.27 (m, 2 H) 3.42 (d, J=13.30 Hz, 4 H) 3.55-3.80 (m, 2 H) 3.93-4.15 (m, 4 H) 4.26 (br. s., 2 H) 4.64 (d, J=13.80 Hz, 2 H) 4.92-5.05 (m, 3 H) 6.60 (d, 1 H) 6.90-7.11 (m, 1 H) 7.28-7.44 (m, 8 H); MS (ESI⁺)=520 M⁺

Example 4

(7R)-N-((R)-1-((S)-4-(4-chlorophenyl)-4-hydroxy-3,3-dimethylpiperidin-1-yl)-3-methyl-1-oxobutan-2-yl)-2-oxo-1-oxa-3-azaspiro[4.4]nonane-7-carboxamide

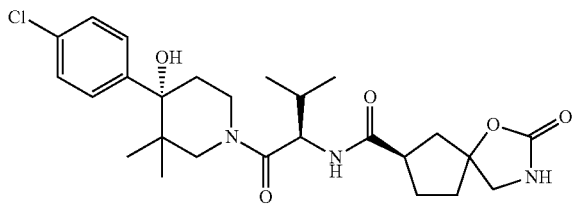 [SMILES: CC(C)[C@@H](NC(=O)[C@@H]1CCC2(CNC(=O)O2)C1)C(=O)N1CC[C@](O)(c2ccc(Cl)cc2)C(C)(C)C1]

Step A: (1R)-benzyl 3-allyl-3-hydroxycyclopentanecarboxylate

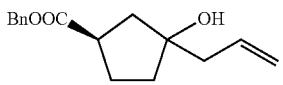

To a solution of (R)-benzyl 3-oxocyclopentanecarboxylate (1 g, 4.58 mmol) in THF (10 mL) was added zinc powder (2.098 mL, 229 mmol), saturated aqueous ammonium chloride solution (20 mL) followed by 3-bromoprop-1-ene (1.663 g, 13.75 mmol) slowly at room temperature. The resulting mixture was heated to 80° C. for 3 hours, then allowed to stir at room temperature for additional 12 hours. The reaction mixture was filtered and the filtrate concentrated. To the residue was added ethyl acetate (20 mL) and the resulting mixture was washed with water (5 ml), brine (5 mL), dried over anhydrous $Na_2SO_4$ and concentrated under reduced pressure to yield (1R)-benzyl 3-allyl-3-hydroxycyclopentanecarboxylate (580 mg, 2.228 mmol, 48.6% yield) as an oil. It was used as such for the next step without further purification. MS (ESI$^+$) m/z 283 (M+Na)$^+$

Step B: 2-((3R)-3-(benzyloxycarbonyl)-1-hydroxycyclopentyl)acetic acid

To a solution of benzyl 3-allyl-3-hydroxycyclopentanecarboxylate (from step A, 150 mg, 0.576 mmol) in ethyl acetate (5 mL) was added ruthenium (IV) oxide hydrate (104 mg, 0.691 mmol) followed by 10% wt. aqueous sodium periodate solution (~3 mL). The resulting mixture was stirred at room temperature for 4 hours. Isopropyl alcohol (3 mL) was added to quench the reaction. The reaction mixture was filtered, and the filtrate was concentrated under reduced pressure to yield 2-(3-(benzyloxycarbonyl)-1-hydroxycyclopentyl)acetic acid (130 mg, 0.467 mmol, 81% yield) as an oil. It was used as such for the next step without further purification. MS (ESI$^+$) m/z 301 (M+Na)$^+$

Step C: (7R)-benzyl 2-oxo-1-oxa-3-azaspiro[4.4]nonane-7-carboxylate

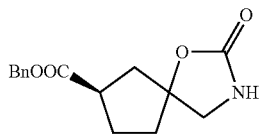

To a solution of 2-((3R)-3-(benzyloxycarbonyl)-1-hydroxycyclopentyl)acetic acid (from step B, 130 mg, 0.467 mmol) in a mixture of toluene (2 mL) and tetrahydrofuran (1.0 mL) was added triethylamine (0.098 mL, 0.701 mmol) and diphenylphosphoryl azide (154 mg, 0.561 mmol) at room temperature. The resulting mixture was heated to 80° C. for 45 min. The reaction mixture was concentrated and the residue was subjected to preparative HPLC (Shimadzu VP-ODS 20×100 mm, 8 min. gradient, Solvent A: 10% MeOH, 90% $H_2O$, 0.1% TFA; Solvent B: 90% MeOH, 10% $H_2O$, 0.1% TFA). The fractions corresponding to the individual diastereomers were collected, concentrated, freeze dried and taken forward individually. Isomer 1: 20 mg, 0.073 mmol, 15.5% yield, MS (ESI$^+$) m/z 276 (M+H)$^+$; Isomer 2: 20 mg, 0.073 mmol, 15.5% yield, MS (ESI$^+$) m/z 276 (M+H)$^+$

Step D: (7R)-2-oxo-1-oxa-3-azaspiro[4.4]nonane-7-carboxylic acid

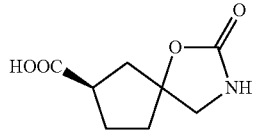 [SMILES: O=C1NCC2(CC[C@@H](C(=O)O)C2)O1]

To a solution of (7R)-benzyl 2-oxo-1-oxa-3-azaspiro[4.4]nonane-7-carboxylate (20 mg, 0.073 mmol) in methanol (3 mL) was added palladium on carbon (10% wt., 15.46 mg, 0.015 mmol). The resulting mixture was stirred under a hydrogen balloon for 30 min. The reaction mixture was filtered and the filtrate was concentrated to yield (7R)-2-oxo-1-oxa-3-azaspiro[4.4]nonane-7-carboxylic acid (13 mg for each isomer, 0.070 mmol, 97% yield) as an oil.

Step E: (7R)-N-((R)-1-((S)-4-(4-chlorophenyl)-4-hydroxy-3,3-dimethylpiperidin-1-yl)-3-methyl-1-oxobutan-2-yl)-2-oxo-1-oxa-3-azaspiro[4.4]nonane-7-carboxamide

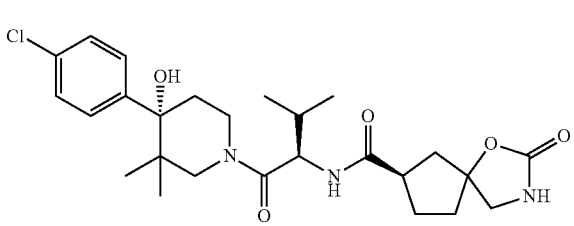 [SMILES: CC(C)[C@@H](NC(=O)[C@@H]1CCC2(CNC(=O)O2)C1)C(=O)N1CC[C@](O)(c2ccc(Cl)cc2)C(C)(C)C1]

To a solution of (R)-2-amino-1-((S)-4-(4-chlorophenyl)-4-hydroxy-3,3-dimethylpiperidin-1-yl)-3-methylbutan-1-one, hydrogen chloride salt (26.3 mg, 0.070 mmol) in THF (1 mL)

was added (7R)-2-oxo-1-oxa-3-azaspiro[4.4]nonane-7-carboxylic acid (13 mg, 0.070 mmol), triethylamine (9.78 μL, 0.070 mmol) and BOP (31.0 mg, 0.070 mmol). The resulting mixture was stirred at room temperature for 4 hours. The reaction mixture was concentrated and the residue was partitioned between ethyl acetate (10 mL) and saturated sodium bicarbonate solution (4 mL). The ethyl acetate layer was concentrated under reduced pressure and the residue was subjected to preparative HPLC (Shimadzu VP-ODS 20×100 mm, 8 min. gradient, Solvent A: 10% MeOH, 90% H2O, 0.1% TFA; Solvent B: 90% MeOH, 10% H2O, 0.1% TFA). The desired fractions were collected, concentrated and freeze dried to yield (7R)-N-((R)-1-((S)-4-(4-chlorophenyl)-4-hydroxy-3,3-dimethylpiperidin-1-yl)-3-methyl-1-oxobutan-2-yl)-2-oxo-1-oxa-3-azaspiro[4.4]nonane-7-carboxamide (15 mg for each isomer, 0.030 mmol, 42.2% yield) as a solid.

Isomer 1: Anal. RP-HPLC: Retention time=3.12 min (YMC S5 ODS 4.6×50 mm; gradient solvent A: 10% MeOH, 90% H$_2$O, 0.2% H$_3$PO$_4$; Solvent B: 90% MeOH, 10% H$_2$O, 0.2% H$_3$PO$_4$); Purity: >95%; MS (ESI$^+$)=506 M;

Isomer 2: Anal. RP-HPLC: Retention time=3.16 min (YMC S5 ODS 4.6×50 mm; gradient solvent A: 10% MeOH, 90% H$_2$O, 0.2% H$_3$PO$_4$; Solvent B: 90% MeOH, 10% H$_2$O, 0.2% H$_3$PO$_4$); Purity: >95%; 1H NMR (400 MHz, CHLOROFORM-d) [rotamers, integration values are assigned based on a 1:1 inseparable mixture of a and b rotamers for a total of 70 protons, excluding the OH proton] δ ppm 0.76 (d, J=2.01 Hz, 6 H) 0.87 (d, J=4.27 Hz, 6 H) 0.95 (td, J=12.42, 6.78 Hz, 9 H) 1.05 (d, J=6.53 Hz, 3 H) 1.49 (d, J=14.31 Hz, 1 H) 1.60 (d, J=14.05 Hz, 1 H) 1.84-2.37 (m, 12 H) 2.56-2.77 (m, J=13.99, 13.83, 13.83, 4.77 Hz, 2 H) 3.11 (d, J=12.80 Hz, 1 H) 3.14-3.28 (m, 1 H) 3.44 (d, J=12.80 Hz, 1 H) 3.53-3.79 (m, 5 H) 4.02 (d, J=11.04 Hz, 1 H) 4.11 (d, J=12.80 Hz, 1 H) 4.56-5.07 (m, 10 H) 6.13-6.36 (m, 1 H) 7.19 (d, J=9.03 Hz, 1 H) 7.28-7.49 (m, 8 H); MS (ESI$^+$)=506 M$^+$ Example 5

(2R)-N((R)-1-((S)-4-(4-chlorophenyl)-4-hydroxy-3,3-dimethylpiperidin-1-yl)-3-methyl-1-oxobutan-2-yl)-7-oxo-6-oxa-8-azaspiro[4.5]decane-2-carboxamide

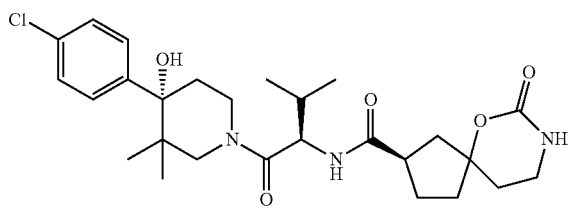 [SMILES: CC(C)[C@@H](NC(=O)[C@@H]1CCC2(CCNC(=O)O2)C1)C(=O)N1CC[C@](O)(c2ccc(Cl)cc2)C(C)(C)C1]

Step A: (1R)-benzyl 3-hydroxy-3-(2-oxoethyl)cyclopentanecarboxylate

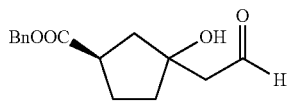

(1R)-benzyl 3-allyl-3-hydroxycyclopentanecarboxylate (from step A, example 04, 200 mg, 0.768 mmol) was dissolved in dichloromethane (5 mL) and ozonized at −78° C. until the blue color persists. The reaction mixture was purged with nitrogen gas until the blue color disappeared. To the reaction mixture was added triethylamine (0.5 mL) and the contents allowed to warm up to room temperature and stirred at room temperature for additional 1 hour. The reaction mixture was passed through a 4 g silica gel cartridge (eluted with ethyl acetate) and the eluant was concentrated under reduced pressure to yield (1R)-benzyl 3-hydroxy-3-(2-oxoethyl)cyclopentanecarboxylate (100 mg, 0.381 mmol, 49.6% yield) as an oil. It was used as such for the next step without further purification.

Step B: (1R)-benzyl 3-(2-aminoethyl)-3-hydroxycyclopentanecarboxylate

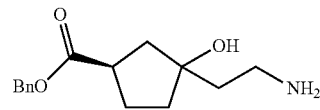 [SMILES: NCCC1(O)CC[C@@H](C(=O)OCc2ccccc2)C1]

To a solution of (1R)-benzyl 3-hydroxy-3-(2-oxoethyl)cyclopentanecarboxylate (from step A, 100 mg, 0.381 mmol) in acetonitrile (2 mL) was added tert-butyl carbamate (134 mg, 1.144 mmol), triethylsilane (133 mg, 1.144 mmol) and trifluoroacetic acid (2.94 μL, 0.038 mmol). The resulting mixture was stirred at room temperature for 4 hours. The reaction mixture was concentrated and treated with hydrogen chloride (4M solution in dioxane, 2 mL) subsequently. After the reaction was stirred at room temperature for 30 min, the reaction mixture was concentrated and subjected to preparative HPLC (Shimadzu VP-ODS 20×100 mm, 8 min. gradient, Solvent A: 10% MeOH, 90% H2O, 0.1% TFA; Solvent B: 90% MeOH, 10% H2O, 0.1% TFA). The desired fractions were collected, concentrated and freeze dried to yield (1R)-benzyl 3-(2-aminoethyl)-3-hydroxycyclopentanecarboxylate, trifluoroacetic acid salt (40 mg, 0.106 mmol, 27.8% yield) as a solid. MS (ESI$^+$)=264 M$^+$ Step C: (2R)-benzyl 7-oxo-6-oxa-8-azaspiro[4.5]decane-2-carboxylate

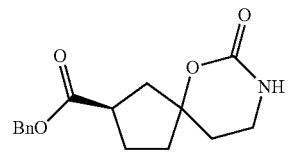 [SMILES: O=C1NCCC2(CC[C@@H](C(=O)OCc3ccccc3)C2)O1]

To a solution of (1R)-benzyl 3-(2-aminoethyl)-3-hydroxycyclopentanecarboxylate, trifluoroacetic acid salt (from step B, 35 mg, 0.093 mmol) in THF (0.5 mL) was added triethylamine (0.026 mL, 0.186 mmol) followed by 1,1'-carbonyldiimidazole (22.56 mg, 0.139 mmol). The resulting mixture was stirred at room temperature for 2 hours. The reaction mixture was concentrated and subjected to preparative HPLC (Shimadzu VP-ODS 20×100 mm, 8 min. gradient, Solvent A: 10% MeOH, 90% H$_2$O, 0.1% TFA; Solvent B: 90% MeOH, 10% H$_2$O, 0.1% TFA). The desired fractions were collected, concentrated and freeze dried to yield (2R)-benzyl 7-oxo-6- oxa-8-azaspiro[4.5]decane-2-carboxylate (22 mg, 0.076 mmol, 82% yield) as a solid. MS (ESI)=312 (M+Na)+

Step D: (2R)-7-oxo-6-oxa-8-azaspiro[4.5]decane-2-carboxylic acid

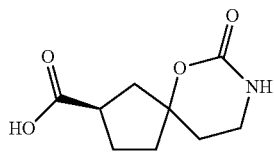

To a solution of (2R)-benzyl 7-oxo-6-oxa-8-azaspiro[4.5]decane-2-carboxylate (from step C, 22 mg, 0.076 mmol) in MeOH (1 mL) was added palladium on carbon (10% wt., 8.09 mg, 7.60 µmol). The resulting mixture was stirred under a hydrogen balloon for 30 min. The reaction mixture was filtered and the filtrate concentrated under reduced pressure to yield (2R)-7-oxo-6-oxa-8-azaspiro[4.5]decane-2-carboxylic acid (15 mg, 0.075 mmol, 99% yield) as an oil. MS =200 (M+H)+

Step E: (2R)-N((R)-1-((S)-4-(4-chlorophenyl)-4-hydroxy-3,3-dimethylpiperidin-1-yl)-3-methyl-1-oxobutan-2-yl)-7-oxo-6-oxa-8-azaspiro[4.5]decane-2-carboxamide

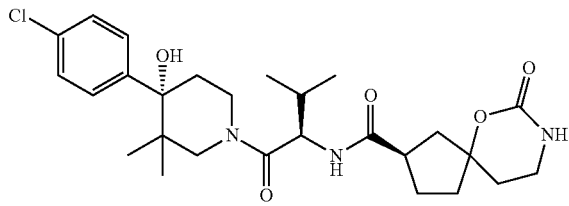 [SMILES: CC(C)[C@@H](NC(=O)[C@@H]1CCC2(CCNC(=O)O2)C1)C(=O)N1CC[C@](O)(c2ccc(Cl)cc2)C(C)(C)C1]

To a solution of (2R)-7-oxo-6-oxa-8-azaspiro[4.5]decane-2-carboxylic acid (from step D, 18 mg, 0.090 mmol) in THF (0.5 mL) was added (R)-2-amino-1-((S)-4-(4-chlorophenyl)-4-hydroxy-3,3-dimethylpiperidin-1-yl)-3-methylbutan-1-one, hydrogen chloride salt (33.9 mg, 0.090 mmol), triethylamine (0.025 mL, 0.181 mmol) and BOP (40.0 mg, 0.090 mmol). The resulting mixture was stirred at room temperature for 16 hours. The reaction mixture was concentrated and subjected to preparative HPLC (Shimadzu VP-ODS 20×100 mm, 8 min. gradient, Solvent A: 10% MeOH, 90% H2O, 0.1% TFA; Solvent B: 90% MeOH, 10% H2O, 0.1% TFA). The desired fractions were collected, concentrated and freeze dried to yield the desired product as a diastereomer mixture. The diastereomer mixture was subjected to chiral preparative HPLC (Column: ChiralPak AD-H, 250×3 cm, 5 µm; Flow rate: 110 mL/min; Mobile Phase: CO2/IPA=65/35; Inj. Vol.=2.0 mL, Wavelength=220 nM; isomer 1, retention time=4.04 min; isomer 2, retention time=13.80 min) to yield the individual isomers (isomer 1: 20 mg, 0.038 mmol, 33.3% yield; isomer 2: 18 mg, 0.035 mmol, 30.0% yield) as a solid. Isomer 1: Anal. RP-HPLC: Retention time=3.07 min (YMC S5 ODS 4.6×50 mm; 4 min gradient, run time 8 min, solvent A: 10% MeOH, 90% H2O, 0.2% H3PO4; Solvent B: 90% MeOH, 10% H2O, 0.2% H3PO4). Purity: >95%; MS (ESI+) m/z 520 M+;

Isomer 2: Anal. RP-HPLC: Retention time=3.14 min (YMC S5 ODS 4.6×50 mm; 4 min gradient, run time 8 min, solvent A: 10% MeOH, 90% H2O, 0.2% H3PO4; Solvent B: 90% MeOH, 10% H2O, 0.2% H3PO4). Purity: >95%; MS (ESI+) m/z 520 M+

Example 6

(3R)-N-((R)-1-((S)-4-(4-chlorophenyl)-4-hydroxy-3,3-dimethylpiperidin-1-yl)-3-methyl-1-oxobutan-2-yl)-3'-methyl-6'-oxo-2',5',6',7'-tetrahydro-spiro[cyclopentane-1,4'-pyrazolo[3,4-b]pyridine]-3-carboxamide

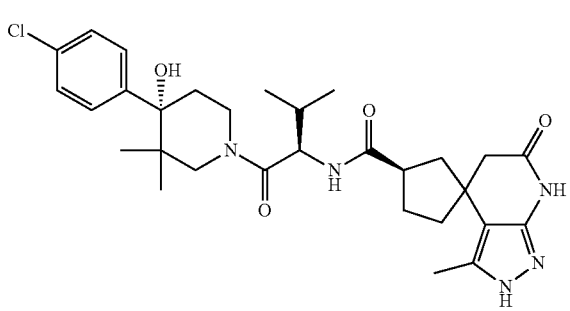 [SMILES: Cc1[nH]nc2c1C1(CC[C@@H](C(=O)N[C@@H](C(=O)N3CC[C@](O)(c4ccc(Cl)cc4)C(C)(C)C3)C(C)C)C1)CC(=O)N2]

Step A: (3R)-benzyl 3'-methyl-6'-oxo-2',5',6',7'-tetrahydrospiro[cyclopentane-1,4'-pyrazolo[3,4-b]pyridine]-3-carboxylate

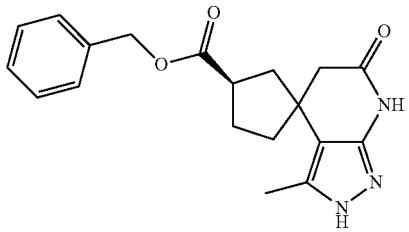 [SMILES: Cc1[nH]nc2c1C1(CC[C@@H](C(=O)OCc3ccccc3)C1)CC(=O)N2]

To (R)-benzyl 3-oxocyclopentanecarboxylate (0.4 g, 1.833 mmol) were sequentially added N-methylpyrrolidone (3 mL), 2,2-dimethyl-1,3-dioxane-4,6-dione (0.264 g, 1.833 mmol) and 3-methyl-1H-pyrazol-5-amine (0.178 g, 1.833 mmol) at room temperature. The contents heated to 80° C. (oil bath temp.) for 75 min, and stirred at room temperature for additional 48 hours. The reaction mixture was partitioned between ethyl acetate (40 mL) and 1N hydrogen chloride (15 mL). The ethyl acetate layer was separated and sequentially washed with 1N sodium hydroxide (15 mL), brine (20 mL), dried over sodium sulfate, concentrated and subjected to preparative HPLC (Phenomex Luna AXIA 30×100 mm; 10 min. gradient; solvent A=10% MeOH, 90% H2O, 0.1% TFA, solvent B=90% MeOH, 10% H2O, 0.1% TFA). Fractions corresponding to the desired product were isolated and concentrated. The residue that was obtained was partitioned between dichloromethane (20 mL) and saturated aqueous sodium bicarbonate solution. The dichloromethane layer was separated, dried over sodium sulfate and concentrated to yield a solid (33 mg, 0.097 mmol, 5.31%). It was used as such for the subsequent step without further purification. MS (ESI) m/z 340.16 (M+H)+

Step B: (3R)-3'-methyl-6'-oxo-2',5',6',7'-tetrahydrospiro[cyclopentane-1,4'-pyrazolo[3,4-b]pyridine]-3-carboxylic acid

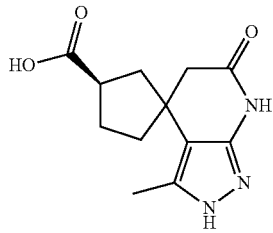 [SMILES: Cc1[nH]nc2c1C1(CC[C@@H](C(=O)O)C1)CC(=O)N2]

To (3R)-benzyl 3'-methyl-6'-oxo-2',5',6',7'-tetrahydrospiro[cyclopentane-1,4'-pyrazolo[3,4-b]pyridine]-3-carboxylate (from step A: 0.033 g, 0.097 mmol) in ethyl acetate (5 mL) was added Pd—C (10% wt., 0.020 g, 0.019 mmol) under a nitrogen atmosphere. The contents were hydrogenated at room temperature using a hydrogen balloon for 1.5 hours. The reaction mixture was concentrated; methanol (5 mL) was added followed by additional Pd—C (0.020 g, 0.019 mmol). The contents were hydrogenated at 25 psi for 1 hour. The reaction mixture was filtered over a Whatman filter (FN MB 25 MM 0.45 uM) paper and washed with methanol (2×10 mL). The filtrate was concentrated under reduced pressure to yield an oil (0.017 g) which was azeotroped with THF (2×10 mL) and used as such for the subsequent step without further purification. MS (ESI) m/z 250.19 (M+H)$^+$ Step C: (3R)-N-((R)-1-((S)-4-(4-chlorophenyl)-4-hydroxy-3,3-dimethylpiperidin-1-yl)-3-methyl-1-oxobutan-2-yl)-3'-methyl-6'-oxo-2',5',6',7'-tetrahydrospiro[cyclopentane-1,4'-pyrazolo[3,4-b]pyridine]-3-carboxamide

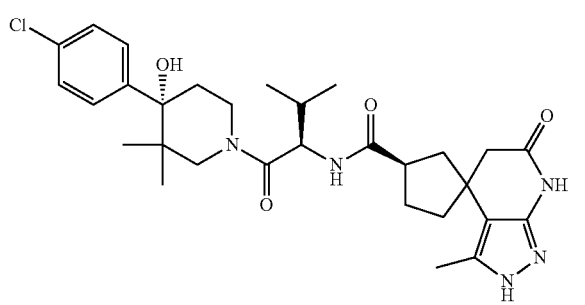 [SMILES: Cc1[nH]nc2c1C1(CC[C@@H](C(=O)N[C@@H](C(=O)N3CC[C@](O)(c4ccc(Cl)cc4)C(C)(C)C3)C(C)C)C1)CC(=O)N2]

To (R)-2-amino-1-((S)-4-(4-chlorophenyl)-4-hydroxy-3,3-dimethylpiperidin-1-yl)-3-methylbutan-1-one, HCl (0.023 g, 0.060 mmol) in DMF (2 mL) were sequentially added (3R)-3'-methyl-6'-oxo-2',5',6',7'-tetrahydrospiro[cyclopentane-1,4'-pyrazolo[3,4-b]pyridine]-3-carboxylic acid (from step B, 0.015 g, 0.060 mmol), N,N-diisopropylethylamine (0.021 mL, 0.120 mmol) and BOP (0.027 g, 0.060 mmol) at room temperature. The reaction mixture was stirred at room temperature for 18 hours.

The reaction mixture was concentrated under reduced pressure (high vacuum pump) and subjected to preparative HPLC (Phenomex Luna AXIA 30×100 mm; 10 min. gradient; solvent A=10% MeOH, 90% H$_2$O, 0.1% TFA, solvent B=90% MeOH, 10% H$_2$O, 0.1% TFA). Fractions corresponding to the desired product were isolated and concentrated. The residue that was obtained was partitioned between dichloromethane (20 mL) and saturated aqueous sodium bicarbonate solution (10 mL). The dichloromethane layer was separated, dried over sodium sulfate and concentrated to yield (3R)-N-((R)-1-((S)-4-(4-chlorophenyl)-4-hydroxy-3,3-dimethylpiperidin-1-yl)-3-methyl-1-oxobutan-2-yl)-3'-methyl-6'-oxo-2',5',6',7'-tetrahydrospiro[cyclopentane-1,4'-pyrazolo[3,4-b]pyridine]-3-carboxamide (0.008 g, 0.014 mmol, 23.32% yield) as a diastereomeric mixture. Anal. RP-HPLC: Retention time=3.24 min (YMC S5 Combi ODS 4.6× 50 mm; 4 min. gradient; solvent A=10% MeOH, 90% H$_2$O, 0.2% H$_3$PO$_4$, solvent B=90% MeOH, 10% H$_2$O, 0.2% H$_3$PO$_4$). Purity: >95%. MS (ESI) m/z 570.31 (M+H)+

Example 7

(7R)-N-((R)-1-((S)-4-(4-chlorophenyl)-4-hydroxy-3,3-dimethylpiperidin-1-yl)-3-methyl-1-oxobutan-2-yl)-2,4-dioxo-1,3-diazaspiro[4.4]nonane-7-carboxamide

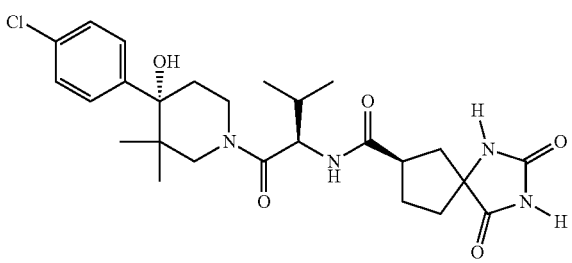 [SMILES: CC(C)[C@@H](NC(=O)[C@@H]1CCC2(C1)NC(=O)NC2=O)C(=O)N1CC[C@](O)(c2ccc(Cl)cc2)C(C)(C)C1]

Step A: (7R)-benzyl 2,4-dioxo-1,3-diazaspiro[4.4]nonane-7-carboxylate

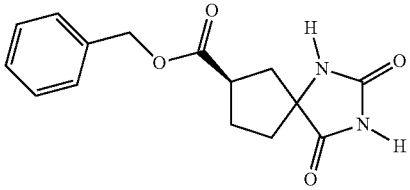 [SMILES: O=C1NC(=O)C2(CC[C@@H](C(=O)OCc3ccccc3)C2)N1]

To (R)-benzyl 3-oxocyclopentanecarboxylate (0.5 g, 2.291 mmol) in ethanol (5 mL) were sequentially added sodium cyanide (0.281 g, 5.73 mmol), ammonium carbonate (2.86 g, 29.8 mmol) and water (5.00 mL) at room temperature. The contents were heated at 70° C. (oil bath temp.) for 3 hours. The reaction mixture was kept at room temperature for 10 min. Solid separates out. The solid was filtered and washed with water (3×10 mL). The solid was dried overnight under vacuum (155 mg, 0.538 mmol, 23.5%) and used as such for the subsequent step without further purification. MS (ESI) m/z 289.16 (M+H)$^+$ Step B: (7R)-2,4-dioxo-1,3-diazaspiro[4.4]nonane-7-carboxylic acid

To (7R)-benzyl 2,4-dioxo-1,3-diazaspiro[4.4]nonane-7-carboxylate (from step A, 0.14 g, 0.486 mmol) in methanol (10 mL) was added Pd—C (0.030 g, 0.282 mmol) under a nitrogen atmosphere. The contents were hydrogenated at 10 psi for 3 hours. The reaction mixture was filtered over a whatman filter (FN MB 25 MM 0.45 uM) paper and washed with methanol (2×5 mL). The filtrate was concentrated under reduced pressure to yield a solid (0.09 g, 0.454 mmol, 94% yield). It was used as such for the subsequent step without further purification. MS m/z 197.3 (M−H)$^+$ Step C: (7R)-N-((R)-1-((S)-4-(4-chlorophenyl)-4-hydroxy-3,3-dimethylpiperidin-1-yl)-3-methyl-1-oxobutan-2-yl)-2,4-dioxo-1,3-diazaspiro[4.4]nonane-7-carboxamide

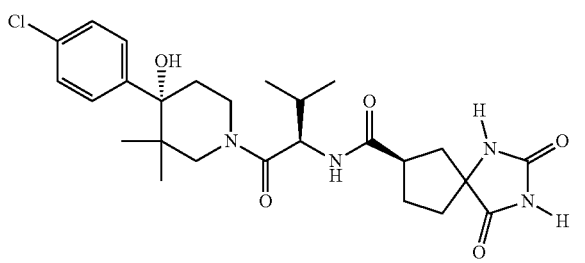

To (R)-2-amino-1-((S)-4-(4-chlorophenyl)-4-hydroxy-3,3-dimethylpiperidin-1-yl)-3-methylbutan-1-one, HCl (from step B, 0.085 g, 0.227 mmol) in THF (2 mL) was sequentially added (7R)-2,4-dioxo-1,3-diazaspiro[4.4]nonane-7-carboxylic acid (step B, 0.045 g, 0.227 mmol), N,N-diisopropylethylamine (0.079 mL, 0.454 mmol) and BOP (0.100 g, 0.227 mmol) at room temperature. The contents were stirred at room temperature for 20 hours. The reaction mixture was subjected to preparative HPLC (Phenomex Luna AXIA 30×100 mm; 10 min. gradient; solvent A=10% MeOH, 90% H2O, 0.1% TFA, solvent B=90% MeOH, 10% H2O, 0.1% TFA) and fractions corresponding to desired product were isolated and concentrated. The residue was partitioned between dichloromethane (20 mL) and saturated aqueous sodium bicarbonate solution (3 mL). The dichloromethane layer was dried over anhydrous sodium sulfate and concentrated to yield a solid (0.095 g, 0.183 mmol, 81% yield). Anal. RP-HPLC: Retention time=3.15 min (YMC S5 Combi ODS 4.6×50 mm; 4 min. gradient; solvent A=10% MeOH, 90% H2O, 0.2% H3PO4, solvent B=90% MeOH, 10% H2O, 0.2% H3PO4); Purity: >95%; mixture of rotamers; MS (ESI) m/z 519 (M+H)$^+$ Example 8

(7R)-N-((R)-1-((S)-4-(4-chlorophenyl)-4-hydroxy-3,3-dimethylpiperidin-1-yl)-3-methyl-1-oxobutan-2-yl)-1-methyl-2,4-dioxo-1,3-diazaspiro[4.4]nonane-7-carboxamide

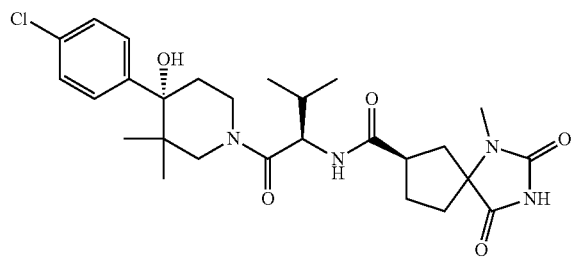 [SMILES: CC(C)[C@@H](NC(=O)[C@@H]1CCC2(C1)C(=O)NC(=O)N2C)C(=O)N1CC[C@](O)(c2ccc(Cl)cc2)C(C)(C)C1]

Step A: (7R)-benzyl 1-methyl-2,4-dioxo-1,3-diazaspiro[4.4]nonane-7-carboxylate

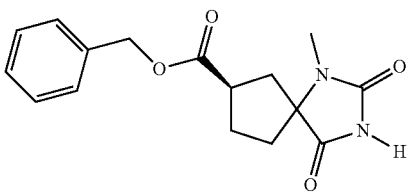 [SMILES: CN1C(=O)NC(=O)C12CC[C@@H](C(=O)OCc1ccccc1)C2]

To (R)-benzyl 3-oxocyclopentanecarboxylate (0.5 g, 2.291 mmol) were sequentially added ethanol (1.0 mL), water (0.5 mL) and methylamine hydrochloride (0.155 g, 2.291 mmol). The contents were stirred at room temperature for 20 min. Then potassium cyanide (0.149 g, 2.291 mmol) was added at room temperature and the contents stirred at room temperature for 60 hours. The reaction mixture was added to 2.3 mL of 1.0N hydrogen chloride taken in a 25 mL round bottom flask at room temperature followed by the addition of 0.23 mL of concentrated hydrogen chloride at room temperature. The reaction mixture was heated to 90° C. for 1 hour. The reaction mixture was concentrated under reduced pressure and partitioned between water (5 mL) and ethyl acetate (15 mL). The ethyl acetate layer was concentrated and subjected to preparative HPLC (Phenomex Luna AXIA 30×100 mm; 10 min. gradient; solvent A=10% MeOH, 90% H2O, 0.1% TFA, solvent B=90% MeOH, 10% H2O, 0.1% TFA). Fractions corresponding to the desired product were concentrated, partitioned between ethyl acetate (15 mL) and saturated aqueous sodium bicarbonate solution (10 mL). The ethyl acetate layer was separated, dried over sodium sulfate and concentrated to yield (7R)-benzyl 1-methyl-2,4-dioxo-1,3-diazaspiro[4.4] nonane-7-carboxylate (0.105 g, 0.347 mmol, 15.16% yield) as an oil. It was used as such for the subsequent step. MS (ESI) m/z 303.14 (M+H)$^+$ Step B: (7R)-1-methyl-2,4-dioxo-1,3-diazaspiro[4.4]
nonane-7-carboxylic acid

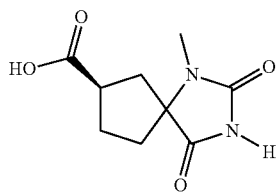

To (7R)-benzyl 1-methyl-2,4-dioxo-1,3-diazaspiro[4.4]nonane-7-carboxylate (from step A, 0.1 g, 0.331 mmol) in ethyl acetate (10 mL) was added Pd—C (0.035 g, 0.033 mmol) under a nitrogen atmosphere. The contents were hydrogenated at 20 psi for 1 hour. The reaction mixture was filtered over a Whatman filter (FN MB 25 MM 0.45 uM) paper and washed with ethyl acetate (2×5 mL). The filtrate was concentrated under reduced pressure to yield an oil (0.05 g, 0.236 mmol, 71.2%) which was used in the next step without further purification. MS m/z 211.3 (M−H)+

Step C: (7R)-N-((R)-1-((S)-4-(4-chlorophenyl)-4-hydroxy-3,3-dimethylpiperidin-1-yl)-3-methyl-1-oxobutan-2-yl)-1-methyl-2,4-dioxo-1,3-diazaspiro[4.4]nonane-7-carboxamide

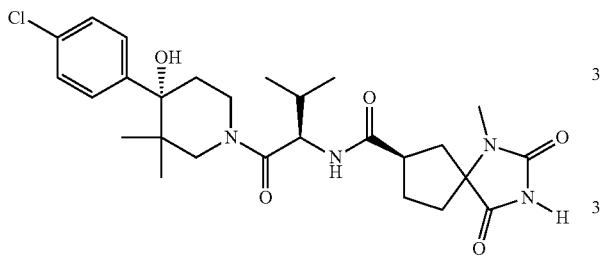

To (R)-2-amino-1-((S)-4-(4-chlorophenyl)-4-hydroxy-3,3-dimethylpiperidin-1-yl)-3-methylbutan-1-one, HCl (0.088 g, 0.236 mmol) in THF (2 mL) were sequentially added (7R)-1-methyl-2,4-dioxo-1,3-diazaspiro[4.4]nonane-7-carboxylic acid (from step B, 0.05 g, 0.236 mmol), N,N-diisopropylethylamine (0.082 mL, 0.471 mmol) and BOP (0.104 g, 0.236 mmol) at room temperature. The contents were stirred at room temperature for 20 hours. The reaction mixture was subjected to preparative HPLC (Phenomex Luna AXIA 30×100 mm; 10 min. gradient; solvent A=10% MeOH, 90% H2O, 0.1% TFA, solvent B=90% MeOH, 10% H2O, 0.1% TFA) and fractions corresponding to the desired product were isolated and concentrated. The residue was partitioned between dichloromethane (20 mL) and saturated aqueous sodium bicarbonate solution (3 mL). The dichloromethane layer was dried over sodium sulfate and concentrated to yield the desired product as a diastereomer mixture. The diastereomer mixture was subjected to chiral preparative HPLC (Column: ChiralPak OD-H, 3×25 cm; Flow rate: 70 mL/min; Mobile Phase: CO2/MeOH=80/20; Wavelength=220 nM; isomer 1, retention time=14.62 min; isomer 2, retention time=21.05 min) to yield the individual isomers (isomer 1: 7 mg, 0.013 mmol, 15.5% yield; isomer 2: 11 mg, 0.021 mmol, 24.4% yield) as a solid.

Isomer 1: Anal. RP-HPLC: Retention time=3.20 min (YMC S5 ODS 4.6×50 mm; 4 min gradient, run time 8 min, solvent A: 10% MeOH, 90% H2O, 0.2% H3PO4; Solvent B: 90% MeOH, 10% H2O, 0.2% H3PO4). Purity: >95%; MS (ESI+) m/z 533.21 M+;

Isomer 2: Anal. RP-HPLC: Retention time=3.15 min (YMC S5 ODS 4.6×50 mm; 4 min gradient, run time 8 min, solvent A: 10% MeOH, 90% H2O, 0.2% H3PO4; Solvent B: 90% MeOH, 10% H2O, 0.2% H3PO4). Purity: >95%; MS (ESI+) m/z 533.23 M+

Example 9

(7R)-3-chloro-N-((R)-1-((S)-4-(4-chlorophenyl)-4-hydroxy-3,3-dimethylpiperidin-1-yl)-3-methyl-1-oxobutan-2-yl)-1-azaspiro[4.4]nonane-7-carboxamide

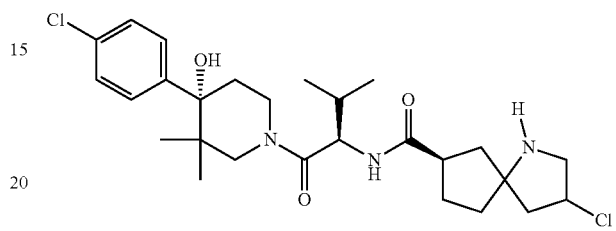

(7R)-N-((R)-1-((S)-4-(4-chlorophenyl)-4-hydroxy-3,3-dimethylpiperidin-4-yl)-3-methyl-1-oxobutan-2-yl)-1-azaspiro[4.4]nonane-7-carboxamide

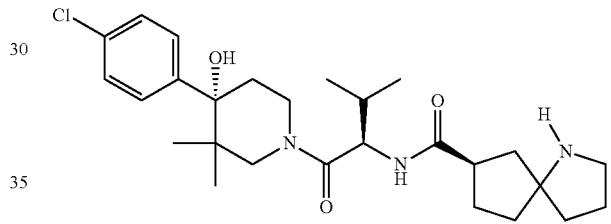

Step A: (7R)-benzyl 3-chloro-1-azaspiro[4.4]nonane-7-carboxylate

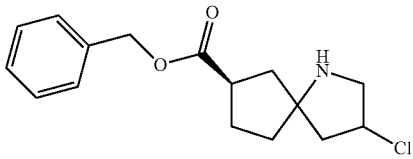

To phenylselenyl chloride (0.199 g, 1.041 mmol) was added (1R)-benzyl 3-allyl-3-aminocyclopentanecarboxylate (example 2, step A, 0.090 g, 0.347 mmol) dissolved in acetonitrile (2 mL). The contents were heated at 80° C. for 18 hours. The reaction mixture was concentrated and partitioned between ethyl acetate (20 mL) and saturated aqueous sodium bicarbonate (10 mL). The ethyl acetate layer was dried over sodium sulfate and concentrated. To the residue was added methanol (5 mL). The solid that separates was filtered and washed with methanol (2 mL). To the filtrate was added 4.0N hydrogen chloride in dioxane (1 mL) and the contents concentrated. Ethyl acetate was added and the resulting mixture was concentrated under reduced pressure. Methanol (5 mL) was added and a solid separates out The liquid was carefully pipetted out into a HPLC vial and subjected to preparative HPLC (Phenomex Luna AXIA 30×100 mm; 10 min. gradient; solvent A=10% MeOH, 90% H2O, 0.1% TFA, solvent B=90% MeOH, 10% H2O, 0.1% TFA). Fractions corresponding to the desired product were isolated and concentrated. The residue was partitioned between dichloromethane (20 mL) and saturated aqueous sodium bicarbonate solution (3 mL). The dichloromethane layer was dried over sodium sulfate and concentrated to yield (7R)-benzyl 3-chloro-1-azaspiro[4.4]nonane-7-carboxylate (0.051 g, 0.174 mmol, 50.0% yield) as an oil. It was used as such for the subsequent step. MS (ESI) m/z 294.14 (M+H)+

Step B: (7R)-1-azaspiro[4.4]nonane-7-carboxylic acid (B-1) and (7R)-3-chloro-1-azaspiro[4.4]nonane-7-carboxylic acid (B-2)

B-1

B-2

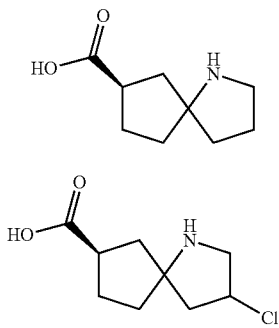

To (7R)-benzyl 3-chloro-1-azaspiro[4.4]nonane-7-carboxylate (from step A, 0.051 g, 0.174 mmol) in methanol (8 mL) was added Pd—C (0.020 g, 0.019 mmol) (10%) under a nitrogen atmosphere. The contents were hydrogenated at 40 psi at room temperature for 3.5 hours. The reaction mixture was filtered over a Whatman filter (FN MB 25 MM 0.45 uM) paper and washed with methanol (2×5 mL). The filtrate was concentrated under reduced pressure to yield a mixture of B-1 and B-2 (0.039 g). It was used as such for the subsequent step without further purification.

Step C: (7R)-3-chloro-N-((R)-1-((S)-4-(4-chlorophenyl)-4-hydroxy-3,3-dimethylpiperidin-1-yl)-3-methyl-1-oxobutan-2-yl)-1-azaspiro[4.4]nonane-7-carboxamide (peak 1 and peak 2) and (7R)-N-((R)-1-((S)-4-(4-chlorophenyl)-4-hydroxy-3,3-dimethylpiperidin-1-yl)-3-methyl-1-oxobutan-2-yl)-1-azaspiro[4.4]nonane-7-carboxamide (peak 3).

Peak 1

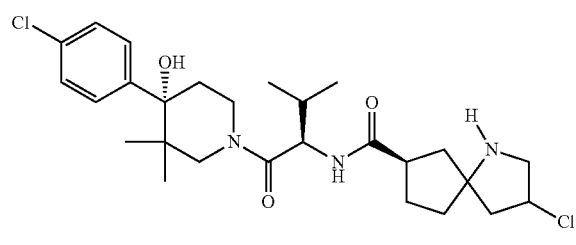 [SMILES: CC(C)[C@@H](NC(=O)[C@@H]1CCC2(CC(Cl)CN2)C1)C(=O)N1CC[C@](O)(c2ccc(Cl)cc2)C(C)(C)C1]

Peak 2

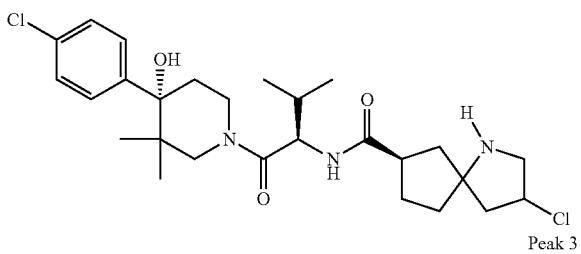

Peak 3

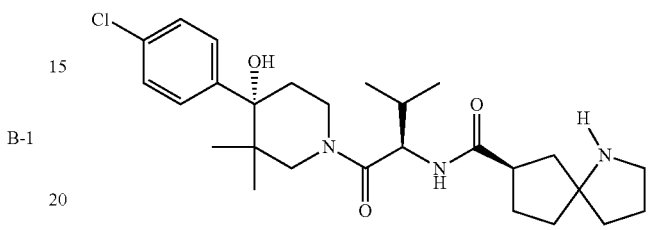

To a mixture of B-1 and B-2 (from step B, 0.039 g, 0.191 mmol) in DMF (1 mL) were sequentially added N,N-diisopropylethylamine (0.100 mL, 0.574 mmol), (R)-2-amino-1-((S)-4-(4-chlorophenyl)-4-hydroxy-3,3-dimethylpiperidin-1-yl)-3-methylbutan-1-one, HCl (0.072 g, 0.191 mmol) and BOP (0.093 g, 0.211 mmol) at room temperature. The contents were stirred at room temperature for 60 hours. The reaction mixture was subjected to preparative HPLC (Phenomex Luna AXIA 30×100 mm; 10 min. gradient; solvent A=10% MeOH, 90% H$_2$O, 0.1% TFA, solvent B=90% MeOH, 10% H$_2$O, 0.1% TFA) and fractions corresponding to the desired products were isolated and concentrated. The residue was partitioned between dichloromethane (20 mL) and saturated aqueous sodium bicarbonate solution (3 mL). The dichloromethane layer was dried over sodium sulfate and concentrated to yield a solid. This solid was subjected to further preparative HPLC separation under the following conditions (Column: Princeton CN, 250×3 cm, 5 μm; Flow rate: 150 mL/min; Mobile Phase: CO$_2$/MeOH+0.1% TEA=88/12; Inj. Vol.=0.5 mL, Wavelength=220 nM; peak 1, retention time=3.83 min; peak 2, retention time=3.98 min; peak 3, retention time=4.11 min) Peaks 1 and 2 correspond to the chloro compound. Peak 3 corresponds to the deschloro compound. Each fraction was individually concentrated (peak 1: 0.014 g, 0.027 mmol, 13.94% yield; peak 2: 0.024 g, 0.046 mmol, 23.89% yield; peak 3: 0.014 g, 0.029 mmol, 14.92% yield).

Peak 1: Anal. RP-HPLC: Retention time=2.86 min (YMC S5 Combi ODS 4.6×50 mm; 4 min. gradient; solvent A=10% MeOH, 90% H$_2$O, 0.2% H$_3$PO$_4$, solvent B=90% MeOH, 10% H$_2$O, 0.2% H$_3$PO$_4$). Purity: >95%.; MS (ESI) m/z 524.29 (M+H)+

Peak 2: Anal. RP-HPLC: Retention time=2.82 min (YMC S5 Combi ODS 4.6×50 mm; 4 min. gradient; solvent A=10% MeOH, 90% H$_2$O, 0.2% H$_3$PO$_4$, solvent B=90% MeOH, 10% H$_2$O, 0.2% H$_3$PO$_4$). Purity: >95%.; MS (ESI) m/z 524.30 (M+H)+

Peak 3: Anal. RP-HPLC: Retention time=2.82 min (YMC S5 Combi ODS 4.6×50 mm; 4 min. gradient; solvent A=10% MeOH, 90% H$_2$O, 0.2% H$_3$PO$_4$, solvent B=90% MeOH, 10% H$_2$O, 0.2% H$_3$PO$_4$. Purity: >95%.; MS (ESI) m/z 490.30 (M+H)+

Example 10

(7R)-1-acetyl-N-((R)-1-((S)-4-(4-chlorophenyl)-4-hydroxy-3,3-dimethylpiperidin-1-yl)-3-methyl-1-oxobutan-2-yl)-1-azaspiro[4.4]nonane-7-carboxamide

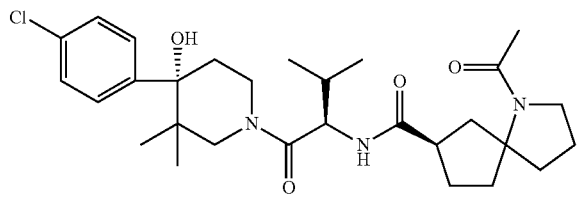 [SMILES: CC(=O)N1CCCC12CC[C@@H](C(=O)N[C@@H](C(=O)N1CC[C@](O)(c3ccc(Cl)cc3)C(C)(C)C1)C(C)C)C2]

To a solution of (7R)-N-((R)-1-((S)-4-(4-chlorophenyl)-4-hydroxy-3,3-dimethylpiperidin-1-yl)-3-methyl-1-oxobutan-2-yl)-1-azaspiro[4.4]nonane-7-carboxamide (from experiment 9, step C, peak 3, 13 mg, 0.027 mmol) in dichloromethane (0.5 mL) was added triethylamine (7.39 μL, 0.053 mmol) and acetic anhydride (4.06 mg, 0.040 mmol). The resulting mixture was stirred at room temperature for 2 hours. The reaction mixture was subjected to preparative HPLC (Shimadzu VP-ODS 20×100 mm, 8 min. gradient, Solvent A: 10% MeOH, 90% H$_2$O, 0.1% TFA; Solvent B: 90% MeOH, 10% H$_2$O, 0.1% TFA). The peak corresponding to the desired product was collected, concentrated and freeze dried to give (7R)-1-acetyl-N-((R)-1-((S)-4-(4-chlorophenyl)-4-hydroxy-3,3-dimethylpiperidin-1-yl)-3-methyl-1-oxobutan-2-yl)-1-azaspiro[4.4]nonane-7-carboxamide (6 mg, 0.011 mmol, 42.5% yield) as a solid. Anal. RP-HPLC: Retention time=3.44 min (YMC S5 ODS 4.6×50 mm; gradient solvent A: 10% MeOH, 90% H$_2$O, 0.2% H$_3$PO$_4$; Solvent B: 90% MeOH, 10% H2O, 0.2% H$_3$PO$_4$). Purity: >95%; MS (ESI) m/z 532 M$^+$

Example 11

N-((R)-1-((S)-4-(4-Chlorophenyl)-4-hydroxy-3,3-dimethylpiperidin-1-yl)-3-methyl-1-oxobutan-2-yl)-1-oxaspiro[2.4]heptane-5-carboxamide

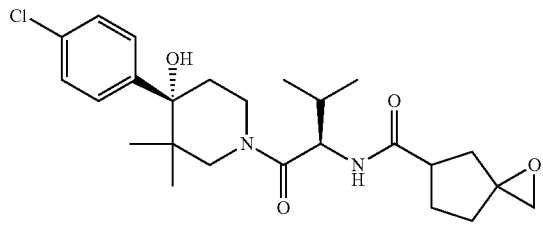 [SMILES: CC(C)[C@@H](NC(=O)C1CCC2(CO2)C1)C(=O)N1CC[C@](O)(c2ccc(Cl)cc2)C(C)(C)C1]

Step A: Ethyl 3-methylenecyclopentanecarboxylate

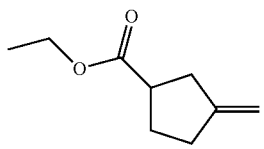

The following reaction was performed in a 15 mL sealed tube, behind a safety shield. To 2-((trimethylsilyl)methyl)allyl acetate (2.227 mL, 10.73 mmol) in toluene (2 mL) was sequentially added ethyl acrylate (2.92 mL, 26.8 mmol), triisopropyl phosphite (1.474 mL, 6.44 mmol) and palladium (II)acetate (0.241 g, 1.073 mmol). The contents were purged with nitrogen gas for 5 min. and heated at 100° C. for 45 h. The reaction mixture was cooled to RT and concentrated under reduced pressure. The liquid was transferred to a 50 mL round bottom flask and distilled using a high vacuum pump. Fractions distilling at 50° C. were collected and concentrated to yield 1.317 g (80%) of ethyl 3-methylenecyclopentanecarboxylate. $^1$H NMR (400 MHz, CDCl$_3$) δ ppm 4.90-4.85 (m, 2 H), 4.14 (q, 2 H, J=7.0 Hz), 2.87-2.78 (m, 1 H), 2.61-2.53 (m, 2 H), 2.51-2.23 (m, 2 H), 2.09-1.82 (m, 2 H), 1.29-1.23 (t, 3 H, J=7.2 Hz).

Step B: Lithium 3-methylenecyclopentanecarboxylate

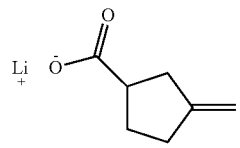

A mixture of ethyl 3-methylenecyclopentanecarboxylate (900 mg, 5.84 mmol) and lithium hydroxide (280 mg, 11.67 mmol) in THF (15 mL) and water (6 mL) was heated at 65° C. for 18 hours. Analysis by TLC indicated that the starting ester had been completely consumed. The organic solvents were removed via rotary evaporator, and the remaining aqueous solution was freeze-dried to yield lithium 3-methylenecyclopentanecarboxylate. $^1$H NMR (400 MHz, CD$_3$OD) δ ppm 4.84-4.73 (m, 2 H), 2.71-2.59 (m, 1 H), 2.57-2.35 (m, 3 H), 2.29-2.16 (m, 1 H), 2.01-1.91 (1 H, m), 1.84-1.72 (m, 1 H,).

Step C: N-((R)-1-((S)-4-(4-Chlorophenyl)-4-hydroxy-3,3-dimethylpiperidin-1-yl)-3-methyl-1-oxobutan-2-yl)-3-methylenecyclopentanecarboxamide

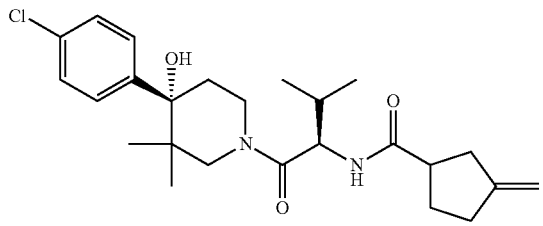 [SMILES: C=C1CCC(C(=O)N[C@@H](C(=O)N2CC[C@](O)(c3ccc(Cl)cc3)C(C)(C)C2)C(C)C)C1]

A mixture of lithium 3-methylenecyclopentanecarboxylate (0.770 g, 5.83 mmol), and Hunig's base (3.56 mL, 20.40 mmol) in DMF (10 mL) was treated with (R)-2-amino-1-((S)-4-(4-chlorophenyl)-4-hydroxy-3,3-dimethylpiperidin-1-yl)-3-methylbutan-1-one, HCl (2.188 g, 5.83 mmol), then BOP (2.84 g, 6.41 mmol), and the mixture was stirred at room temperature for 2 hours. The reaction mixture was poured into 85:15 ethyl acetate/hexanes (200 mL), and the cloudy solution was washed 3× with water, and once with brine. The organic phase was dried over sodium sulfate and concentrated in vacuo. The residue was purified via MPLC over a 40 g silica gel column, eluting at 40 mL/min with 20% then 55% ethyl acetate/hexanes to yield N-((R)-1-((S)-4-(4-chlorophenyl)-4-hydroxy-3,3-dimethylpiperidin-1-yl)-3-methyl-1-oxobutan-2-yl)-3-methylenecyclopentanecarboxamide (1.89 g, 4.23 mmol, 72.5% yield) as a glass. $^1$H NMR (400 MHz, CD$_3$OD) (NMR shows several rotomers) δ ppm 7.49 (d, 1 H, J=8.8 Hz), 7.46 (d, 1 H, J=8.4 Hz), 7.34-7.27 (m, 2 H), 4.86-4.82 (m, 2 H+H$_2$O), 4.60-4.51 (m, 0.7 H), 4.13-4.00 (m, 0.4 H+residual ethyl acetate), 3.66-3.55 (m, 1 H), 3.52 (d, 0.6 H, J=12.7 Hz), 3.17 (td, 0.6 H, J=13.1, 2.9 Hz), 3.11 (d, 0.5 H, J=12.3 Hz), 2.90-2.78 (m, 1 H), 2.70 (td, 0.5 H, J=13.6, 4.8 Hz), 2.61 (td, 0.7 H, J=13.5, 5.1 Hz), 2.56-2.40 (m, 3 H), 2.39-2.22 (m, 1 H), 2.16 (dddd, 0.5 H, J=13.7, 6.8, 6.7, 6.6 Hz), 2.09-1.67 (m, 2.7H+residual ethyl acetate), 1.60 (d, 0.5 H, J=14.1 Hz), 1.51 (d, 0.5 H, J=13.6 Hz), 1.32 (d, 0.6 H, J=5.7 Hz), 1.04 (d, 1.4 H, J=6.6 Hz), 0.99 (dd, 1.4 H, J=6.8, 1.1 Hz), 0.92 (d, 3.2 H, J=6.6 Hz), 0.81 (d, 3 H, J=4.8 Hz), 0.75 (d, 3 H, J=4.8 Hz).
LCMS Method:
  Injection Volume: 10 µL; Start % B=50; Final % B=100
  Gradient Time=4 minutes; Flow Rate=4 mL/minute; Wavelength=220 nM
  Solvent A=10:90 methanol:water+0.1% TFA; Solvent B=90:10 methanol:water+0.1% TFA; Column=Waters Sunfire C18 4.6×50 mm
  Retention Time=3.10 minutes
  MS (ESI$^+$)=448.1 (M+H)$^+$.

Step D Example 11

A mixture of N-((R)-1-((S)-4-(4-chlorophenyl)-4-hydroxy-3,3-dimethylpiperidin-1-yl)-3-methyl-1-oxobutan-2-yl)-3-methylenecyclopentanecarboxamide (535 mg, 1.197 mmol) and sodium bicarbonate (141 mg, 1.676 mmol) in methylene chloride (4 mL) and water (2 mL) was cooled to 5° C. and treated with m-CPBA (318 mg, 1.436 mmol). The mixture was stirred at 5° C. for 1 hour, then allowed to warm to room temperature and stirred for 18 hours. The mixture was cooled to 5° C., treated with saturated sodium sulfite, and stirred at room temperature for 30 minutes. The layers were separated, and the aqueous phase was extracted 3× with methylene chloride. The organic phases were combined and concentrated in vacuo, and the residue was taken up in ethyl acetate. The solution was washed 3× with saturated sodium carbonate, once with water, and once with brine, then dried over sodium sulfate, and concentrated in vacuo to yield the title compound (535 mg, 1.155 mmol, 97% yield) as a glass and a mixture of diastereomers. $^1$H NMR (400 MHz, CD$_3$OD) (NMR shows several rotomers) δ ppm 7.54-7.40 (m, 2 H), 7.37-7.26 (m, 2 H), 4.90-4.82 (m, 1 H+H$_2$O), 4.63-4.48 (m, 0.6 H), 4.12-3.96 (m, 1 H+residual ethyl acetate), 3.68-3.46 (m, 1.6 H), 3.23-3.02 (m, 1.6 H), 2.98-2.90 (m, 0.4 H), 2.90-2.77 (m, 2 H), 2.76-2.53 (m, 1 H), 2.31-1.79 (m, 6 H+residual ethyl acetate), 1.79-1.64 (m, 1.6 H), 1.60 (bd, 0.4 H, J=14.1 Hz), 1.57-1.48 (m, 0.6 H), 1.04 (dd, 1.4 H, J=6.6, 3.1 Hz), 1.00 (t, 1.6 H, J=6.4 Hz), 0.96-0.90 (m, 3.2 H), 0.87-0.79 (dd, 3 H, J=5.5, 3.0 Hz), 0.79-0.71 (m, 3 H).
LCMS Method:
  Start % B=0; Final % B=95; Gradient Time=2 minutes
  Flow Rate=4 mL/minute; Wavelength=220 nM
  Solvent A=10:90 acetonitrile:water+NH$_4$OAc; Solvent B=90:10 acetonitrile:water+NH$_4$OAc; Column=Phenomenex Luna C18 4.6×30 mm 3µ
  Retention Time=0.92 minutes
  MS (ESI$^+$)=463.1 (M+H)$^+$.

Example 12

N-((R)-1-((S)-4-(4-Chlorophenyl)-4-hydroxy-3,3-dimethylpiperidin-1-yl)-3-methyl-1-oxobutan-2-yl)-1-oxaspiro[3.4]octane-6-carboxamide

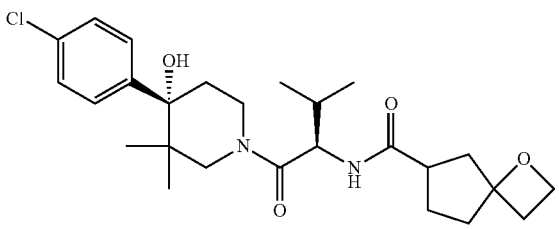 [SMILES: CC(C)[C@@H](NC(=O)C1CCC2(CCO2)C1)C(=O)N1CC[C@](O)(c2ccc(Cl)cc2)C(C)(C)C1]

A suspension of trimethylsulfoxonium iodide (67.8 mg, 0.308 mmol) in tert-butanol (2 mL) was treated with potassium tert-butoxide (34.6 mg, 0.308 mmol). The mixture was heated at 50° C. for 1 hour, then treated with N-((R)-1-((S)-4-(4-chlorophenyl)-4-hydroxy-3,3-dimethylpiperidin-1-yl)-3-methyl-1-oxobutan-2-yl)-1-oxaspiro[2.4]heptane-5-carboxamide (46 mg, 0.099 mmol), and the reaction was stirred at 50° C. for 2 days. The reaction was quenched with saturated ammonium chloride (1 mL), and the mixture was poured into ethyl acetate (15 mL). The layers were separated, and the organic phase was washed 3× with water and once with brine, then dried over sodium sulfate and concentrated in vacuo. The crude material was purified via preparative LC/MS with the following conditions: Column. Waters SunFire C18, 19×150 mm, 5-µm particles; Guard Column. None; Mobile Phase A: 5:95 acetonitrile:water with 10-mM ammonium acetate; Mobile Phase B: 95:5 acetonitrile:water with 10-mM ammonium acetate; Gradient: 15-100% B over 15 minutes, then a 5-minute hold at 100% B; Flow: 20 mL/min. Fractions containing the desired product were combined and dried via centrifugal evaporation. The yield of the desired product as a diastereomeric mixture was 15.4 mg, and its purity was 96%. Two analytical LC/MS injections were used to determine the final purity. Injection 1 conditions: Column: Supelco Ascentis Express C18, 4.6×50 mm, 2.7-µm particles; Mobile Phase A: 5:95 acetonitrile:water with 10 mM ammonium acetate; Mobile Phase B: 95:5 acetonitrile:water with 10 mM ammonium acetate; Temperature: 45° C.; Gradient: 0-100% B over 5.3 minutes, then a 1.7-minute hold at 100% B; Flow: 3 mL/min. Retention time=2.91. Injection 2 conditions: Column: Waters XBridge C18, 4.6×50 mm, 2.5-1 µm particles; Mobile Phase A: 5:95 acetonitrile:water with 0.1% ammonium hydroxide; Mobile Phase B: 95:5 acetonitrile:water with 0.1% ammonium hydroxide; Temperature: 45° C.; Gradient: 0-100% B over 7 minutes, then a 1-minute hold at 100% B; Flow: 3 mL/min. Retention time=3.79 minutes. Proton NMR was acquired in deuterated methanol. MS (ESI$^+$)=476.9 (M+H)$^+$. $^1$H NMR (400 MHz, CD$_3$OD) (NMR shows several rotomers) δ ppm 7.53-7.42 (m, 2 H), 7.36-7.26 (m, 2 H), 4.83-4.76 (m, 1 H), 4.58-4.42 (m, 2 H), 4.13-3.98 (m, 1 H), 3.66-3.58 (bd, 1 H, J=13.3 Hz), 3.58-3.46 (m, 1 H), 3.22-3.06 (m, 1 H), 2.95-2.86 (m, 0.4H), 2.83-2.56 (m, 3.2 H), 2.38-1.69 (m, 7 H), 1.59 (d, 0.5 H, J=14.3 Hz), 1.51 (d, 0.5 H, J=14.6 Hz), 1.47-1.42 (m, 0.2 H), 1.04 (d, 1.5 H, J=6.5 Hz), 0.98 (t, 1.5 H, J=6.2 Hz), 0.92 (d, 3 H, J=5.3 Hz), 0.81 (d, 3 H, J=4.8 Hz), 0.75 (br. s, 3 H.).

Utility

In general, compounds of the present invention, such as particular compounds disclosed in the preceding examples, have been shown to be modulators of chemokine receptor activity (for example, by displaying Ki values<10,000 nM in a binding assay such as those set forth below). By displaying activity as modulators of chemokine receptor activity, compounds of the present invention are expected to be useful in the treatment of human diseases associated with chemokines and their cognate receptors.

CCR1 Ligand Binding Scintillation Proximity Assay (SPA)

For radioligand competition studies, a final concentration of $1\times10^5$ THP-1 monocytic leukemia cells are combined with 100 μg of LS WGA PS beads (Amersham, Cat.#: RPNQ 0260) in 40 μl of assay buffer (RPMI 1640 without phenol red, 50 mM HEPES, 5 mM $MgCl_2$, 1 mM $CaCl_2$, 0.1% BSA). The THP-1 cell/bead mixture is added to each well of a 384-well assay plate (PerkinElmer, Cat. #:6007899) containing test compound in 3-fold serial dilution, with final concentrations ranging from 8 μM to 140 pM. A final concentration of 0.1 nM [$^{125}$I]-MIP-1α (PerkinElmer, Cat. #NEX298) in 20 μl assay buffer is added to the reaction. Sealed assay plates are incubated at room temperature for 12 h then analyzed by LEADseeker™.

The competition data of compound (I) over a range of concentrations is plotted as percentage inhibition of radioligand specific bound in the absence of test compound (percent of total signal). After correcting for non-specific binding, $IC_{50}$ values are determined. The $IC_{50}$ value is defined as the concentration of test compound needed to reduce [$^{125}$I]-MIP-1α specific binding by 50% and is calculated using the four parameter logistic equation to fit the normalized data. The Ki values are determined by application of the Cheng-Prusoff equation to the $IC_{50}$ values, where $K_i=IC_{50}/(1+\text{ligand concentration}/K_d)$ The Kd of [$^{125}$I]-MIP-1α in THP-1 cells is 0.1 nM. Each experiment is run in duplicate.

Compounds of the present invention were tested in the assay described above and the results are shown in Table 1.

TABLE 1

| Example | CCR1 Binding Ki |
|---|---|
| 3-Isomer 2 | 2.4 nM |
| 5-Isomer 2 | 6.6 nM |
| 9-Peak 3 | 193 nM |

Mammalian chemokine receptors provide a target for interfering with or promoting immune cell function in a mammal, such as a human. Compounds that inhibit or promote chemokine receptor function are particularly useful for modulating immune cell function for therapeutic purposes.

Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjorgren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematological malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., Toxocara), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurysm, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes mellitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

In another aspect, the compounds are used to treat or prevent inflammatory disorders selected from rheumatoid arthritis, osteoarthritis, atherosclerosis, aneurysm, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal anti-inflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors; (j) cholesterol lowering agents such as HMG-COA reductase inhibitors (lovastatin, simvastatin and pravastatin, fluvastatin, atorvastatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone and pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (n) other compound such as 5-aminosalicylic acid an prodrugs thereof, anti-metabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

While the invention has been described in detail and with reference to specific embodiments thereof, it will be apparent to one skilled in the art that various changes and modifications can be made therein without departing from the spirit and scope thereof.

What is claimed is:

1. A compound, or a stereoisomer or pharmaceutically acceptable salt form thereof, wherein the compound is selected from (2R)-N-((R)-1-((S)-4-(4-chlorophenyl)-4-hydroxy-3,3-dimethylpiperidin-1-yl)-3-methyl-1-oxobutan-2-yl)-7-oxo-6,8-diazaspiro[4.5]decane-2-carboxamide, (7R)-N-((R)-1-((S)-4-(4-chlorophenyl)-4-hydroxy-3,3-dimethylpiperidin-1-yl)-3-methyl-1-oxobutan-2-yl)-2-oxo-1-oxa-3-azaspiro[4.4]nonane-7-carboxamide;

(3R)-N-((R)-1-((S)-4-(4-chlorophenyl)-4-hydroxy-3,3-dimethylpiperidin-1-yl)-3-methyl-1-oxobutan-2-yl)-3'-methyl-6'-oxo-2',5',6',7'-tetrahydro-spiro[cyclopentane-1,4'-pyrazolo[3,4-b]pyridine]-3-carboxamide, (7R)-N-((R)-1-((S)-4-(4-chlorophenyl)-4-hydroxy-3,3-dimethylpiperidin-1-yl)-3-methyl-1-oxobutan-2-yl)-2,4-dioxo-1,3-diazaspiro[4.4]nonane-7-carboxamide, (7R)-N-((R)-1-((S)-4-(4-chlorophenyl)-4-hydroxy-3,3-dimethylpiperidin-1-yl)-3-methyl-1-oxobutan-2-yl)-1-methyl-2,4-dioxo-1,3-diazaspiro[4.4]nonane-7-carboxamide, (7R)-3-chloro-N-((R)-1-((S)-4-(4-chlorophenyl)-4-hydroxy-3,3-dimethylpiperidin-1-yl)-3-methyl-1-oxobutan-2-yl)-1-azaspiro[4.4]nonane-7-carboxamide, (7R)-1-acetyl-N-((R)-1-((S)-4-(4-chlorophenyl)-4-hydroxy-3,3-dimethylpiperidin-1-yl)-3-methyl-1-oxobutan-2-yl)-1-azaspiro[4.4]nonane-7-carboxamide, N-((R)-1-((S)-4-(4-Chlorophenyl)-4-hydroxy-3,3-dimethylpiperidin-1-yl)-3-methyl-1-oxobutan-2-yl)-1-oxaspiro[2.4]heptane-5-carboxamide, and N-((R)-1-((S)-4-(4-Chlorophenyl)-4-hydroxy-3,3-dimethylpiperidin-1-yl)-3-methyl-1-oxobutan-2-yl)-1-oxaspiro[3.4]octane-6-carboxamide.

2. A pharmaceutical composition comprised of a pharmaceutically acceptable carrier and a therapeutically effective amount of one or more compound of claim 1.

* * * * *